United States Patent
Burke et al.

(10) Patent No.: US 10,804,064 B2
(45) Date of Patent: Oct. 13, 2020

(54) MAGNETIC LIFT DEVICE FOR AN X-RAY TUBE

(71) Applicant: Varex Imaging Corporation, Salt Lake City, UT (US)

(72) Inventors: James E. Burke, Salt Lake City, UT (US); Marina Samuels, West Jordan, UT (US); Santosh Ramachandran, Salt Lake City, UT (US); V. Ward Coon, Salt Lake City, UT (US); Christopher J. Lewis, Kaysville, UT (US); Christopher D. Ginzton, Salt Lake City, UT (US); Gregory C. Andrews, West Jordan, UT (US); Patrick K. Lewis, West Jordan, UT (US); Jacob Sullivan, Syracuse, UT (US)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 242 days.

(21) Appl. No.: 15/464,142

(22) Filed: Mar. 20, 2017

(65) Prior Publication Data
US 2017/0301504 A1    Oct. 19, 2017

Related U.S. Application Data

(60) Provisional application No. 62/310,668, filed on Mar. 18, 2016.

(51) Int. Cl.
*H01J 35/10* (2006.01)
*A61B 6/03* (2006.01)
(Continued)

(52) U.S. Cl.
CPC ............ *H01J 35/101* (2013.01); *A61B 6/032* (2013.01); *A61B 6/4435* (2013.01); *H01J 35/06* (2013.01);
(Continued)

(58) Field of Classification Search
CPC ....... H01J 2235/1006; H01J 2235/1026; H01J 2235/1073; H01J 2235/1046;
(Continued)

(56) References Cited

U.S. PATENT DOCUMENTS 4,081,707 A * 3/1978 Hartl ................... F16C 32/0489
378/132
4,166,261 A * 8/1979 Meinke ............... F16C 32/0448
335/246
(Continued)

FOREIGN PATENT DOCUMENTS

JP    S59 151735 A    8/1984
JP    H04-359851 A    12/1992
(Continued)

OTHER PUBLICATIONS

Machine Translation of JP 2009245594.*
(Continued)

*Primary Examiner* — David J Makiya
*Assistant Examiner* — Soorena Kefayati
(74) *Attorney, Agent, or Firm* — Maschoff Brennan

(57) ABSTRACT

Technology is described for a magnetic lift device for an x-ray tube. In one example, an anode assembly includes an anode, a bearing assembly, a ferromagnetic shaft, and a lift electromagnet. The anode is configured to receive electrons emitted by a cathode. The bearing assembly is configured to stabilize the anode during a rotation of the anode. The ferromagnetic shaft is coupled to the anode and has an axis of rotation that is substantially collinear with an axis of
(Continued)

rotation of the anode. The lift electromagnet is configured to apply a magnetic force to the ferromagnetic shaft in a radial direction.

25 Claims, 27 Drawing Sheets

(51) Int. Cl.
*A61B 6/00* (2006.01)
*H01J 35/06* (2006.01)
*H05G 1/30* (2006.01)

(52) U.S. Cl.
CPC ............... *H01J 2235/1006* (2013.01); *H01J 2235/1013* (2013.01); *H01J 2235/1026* (2013.01); *H01J 2235/1046* (2013.01); *H05G 1/30* (2013.01)

(58) Field of Classification Search
CPC ... H01J 35/101; H01J 35/103; F05D 2250/75; F16C 2380/16; F16C 39/16; F16C 32/0485; F16C 32/0487; F16C 32/0476
See application file for complete search history.

(56) References Cited

U.S. PATENT DOCUMENTS

| | | | | |
|---|---|---|---|---|
| 4,322,624 A * | 3/1982 | Cornelissen | ....... | F16C 32/0465 378/125 |
| 4,468,801 A * | 8/1984 | Sudo | ............ | F16C 32/0474 378/130 |
| 4,500,142 A * | 2/1985 | Brunet | ............ | F16C 32/047 310/90.5 |
| 4,504,965 A * | 3/1985 | Ebersberger | ..... | F16C 32/044 378/125 |
| 4,597,613 A * | 7/1986 | Sudo | ............ | F16C 32/0465 310/90.5 |
| 4,608,707 A * | 8/1986 | Gabbay | ............ | H01J 35/103 378/122 |
| 4,941,363 A * | 7/1990 | Doemens | ......... | G01L 3/106 361/290 |
| 4,983,870 A * | 1/1991 | McSparran | ..... | F16C 32/0459 310/216.021 |
| 5,216,308 A * | 6/1993 | Meeks | ............ | F16C 32/0459 310/90.5 |
| 5,357,552 A * | 10/1994 | Kutschera | ....... | F16C 23/08 378/125 |
| 5,729,066 A * | 3/1998 | Soong | ............ | F16C 32/0451 310/51 |
| 5,991,361 A * | 11/1999 | Bhatt | ............ | F16C 25/083 378/125 |
| 6,198,803 B1 * | 3/2001 | Osama | ............ | F16C 32/047 378/125 |
| 6,335,512 B1 * | 1/2002 | Warren | ............ | B23K 31/02 219/137 WM |
| 6,430,262 B1 * | 8/2002 | Panasik | ............ | F16C 25/083 378/121 |
| 6,693,990 B1 * | 2/2004 | Andrews | ........... | H01J 35/101 378/119 |
| 6,762,522 B2 * | 7/2004 | Steinmeyer | ...... | F16C 32/0438 310/90.5 |
| 7,343,002 B1 * | 3/2008 | Lee | ............ | F16C 33/66 378/121 |
| 8,058,758 B2 * | 11/2011 | Ries | ............ | F16C 32/0414 310/90.5 |
| 8,169,118 B2 * | 5/2012 | Filatov | ............ | F16C 32/0465 310/178 |
| 2006/0133578 A1 * | 6/2006 | Saint-Martin | ........ | H01J 9/00 378/132 |
| 2007/0041488 A1 | 2/2007 | Hoheisel et al. | | |
| 2008/0137811 A1 * | 6/2008 | Gadre | ............ | F16J 15/43 378/123 |
| 2009/0016489 A1 * | 1/2009 | Danz | ............ | H01J 35/101 378/94 |
| 2009/0080616 A1 * | 3/2009 | Yoshii | ............ | H01J 35/101 378/133 |
| 2009/0140681 A1 * | 6/2009 | Hauttmann | ....... | G01P 3/44 318/490 |
| 2009/0295244 A1 * | 12/2009 | Ries | ............ | F16C 32/0414 310/90.5 |
| 2010/0194224 A1 * | 8/2010 | Smithanik | ........ | F16C 32/0461 310/90.5 |
| 2010/0260323 A1 * | 10/2010 | Legall | ............ | H01J 35/101 378/125 |
| 2010/0322383 A1 * | 12/2010 | Coon | ............ | H01J 35/103 378/127 |
| 2011/0058654 A1 * | 3/2011 | Tadokoro | ........ | H01J 35/101 378/130 |
| 2012/0038232 A1 * | 2/2012 | Aronstam | ........ | F16C 32/0427 310/90.5 |
| 2012/0106712 A1 * | 5/2012 | Hunt | ............ | H01J 35/101 378/132 |
| 2013/0034214 A1 * | 2/2013 | Luebcke | ............ | H01J 35/101 378/132 |
| 2014/0314208 A1 * | 10/2014 | Foellmer | ........ | H01J 35/10 378/135 |
| 2015/0117604 A1 * | 4/2015 | Chrost | ............ | H01J 35/101 378/62 |
| 2015/0124937 A1 * | 5/2015 | Chrost | ............ | H01J 35/101 378/131 |
| 2015/0211575 A1 * | 7/2015 | Kim | ............ | H01F 27/08 310/90.5 |
| 2016/0108967 A1 * | 4/2016 | Massini | ............ | F16C 37/005 310/90.5 |
| 2016/0215817 A1 * | 7/2016 | Mei | ............ | F16C 32/047 |
| 2017/0148606 A1 * | 5/2017 | Hirayama | ........ | A61B 6/032 |

FOREIGN PATENT DOCUMENTS

| | | | |
|---|---|---|---|
| JP | 2003-009481 A | | 1/2003 |
| JP | 2005-206337 A | | 8/2005 |
| JP | 2009-021161 A | | 1/2009 |
| JP | 2009-245594 A | | 10/2009 |
| JP | 2009245594 A | * | 10/2009 |
| JP | 2012-099465 A | | 5/2012 |

OTHER PUBLICATIONS

Machine Translation of JP 2009245594 (Year: 2009).*
English translation of JP-2009245594-A. (Year: 2020).*
International Search Report and Written Opinion dated Jun. 13, 2017, in related PCT Application No. PCT/US2017/023238.
European Search Report dated Sep. 13, 2019, in European Patent Application No. 17767707.7.
Supplementary EP Search Report dated Jan. 13, 2020, for related European Patent Application No. 17767707.7 (16 pgs.).

* cited by examiner

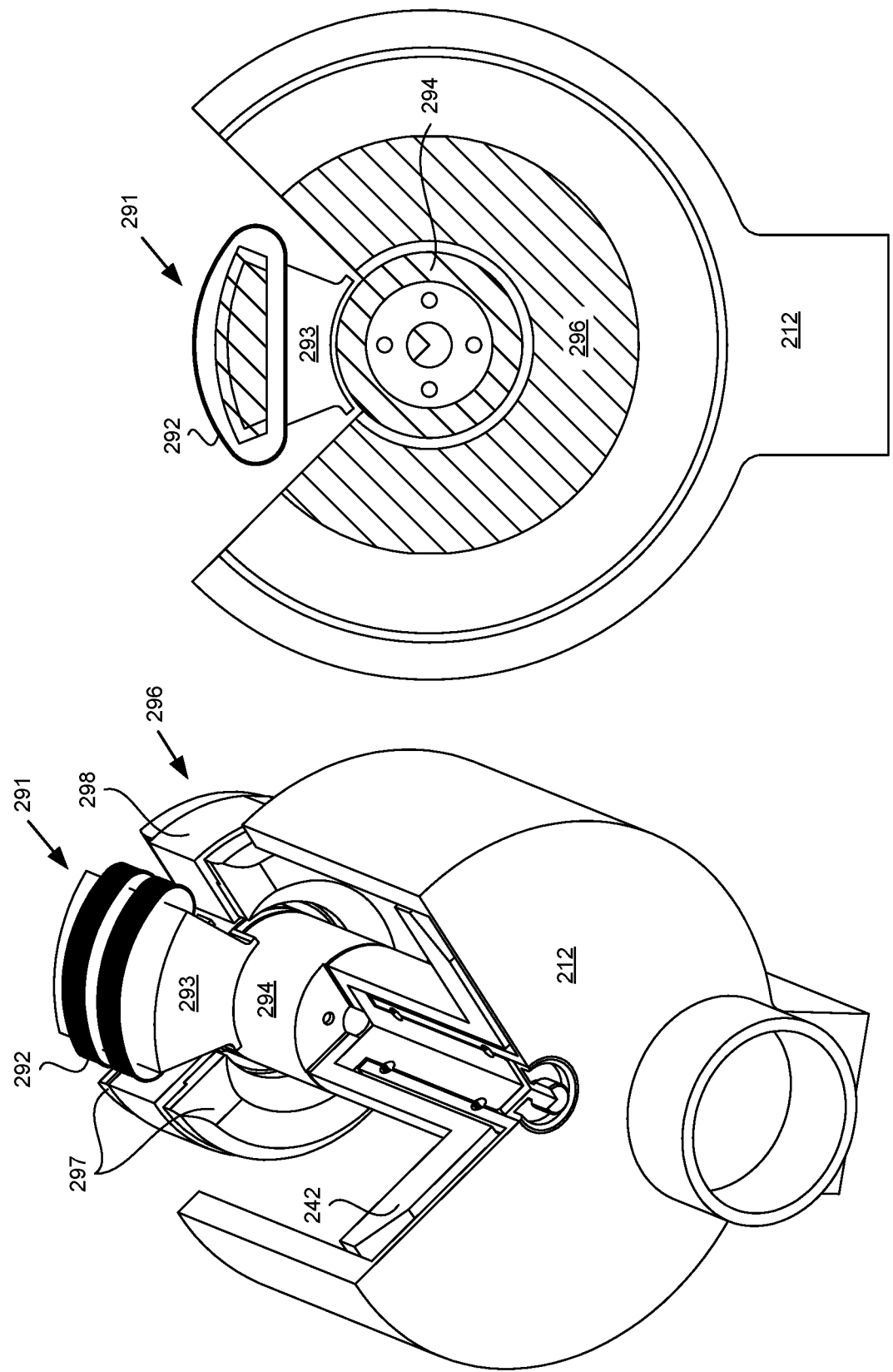

MAGNETIC LIFT DEVICE FOR AN X-RAY TUBE

BACKGROUND

Unless otherwise indicated herein, the approaches described in this section are not prior art to the claims in this disclosure and are not admitted to be prior art by inclusion in this section.

An x-ray system typically includes an x-ray tube and a detector. The power and signals for the x-ray tube can be provided by a high voltage generator. The x-ray tube emits radiation, such as x-rays, toward an object. The object is positioned between the x-ray tube and the detector. The radiation typically passes through the object and impinges on the detector. As radiation passes through the object, internal structures of the object cause attenuation in the radiation received at the detector. The detector then generates data based on the detected radiation, and the system translates the radiation variances into an image, which may be used to evaluate the internal structure of the object, such as a patient in a medical imaging procedure or an inanimate object in an inspection scan.

The x-ray tube includes a cathode and an anode. X-rays are produced in x-ray tubes by applying an electrical current to an emitter positioned within the cathode to cause electrons to be emitted from the cathode by thermionic emission. In a vacuum, the electrons accelerate towards and then impinge upon the anode due to the voltage difference between the cathode and the anode. When the electrons collide with a target on the anode, some of the energy is emitted as x-rays, and the majority of the energy is released as heat. The area on the anode in which the electrons collide is generally known as the focal spot, and the emitted x-rays can have a center ray beam (i.e., center ray, center x-ray beam, central ray beam, central ray, or central x-ray beam) emanating from the focal spot representing x-rays with a high intensity. Because of high temperatures generated when the electron beam strikes the target, specifically the focal spot, the anode can include features to distribute the heat generated at the focal spot on the target, such as rotating a disc-shaped anode target at a high rotational speed. A rotating anode typically includes the disc-shaped anode target, which is rotated by an induction motor via a bearing assembly.

The radiation detector (e.g., x-ray detector) can include a conversion element that converts an incoming radiation beam into electrical signals, which can be used to generate data about the radiation beam, which in turn can be used to characterize an object being inspected (e.g., the patient or inanimate object). In one example, the conversion element includes a scintillator that converts a radiation beam into light, and a sensor that generates electrical signals in response to the light. The detector can also include processing circuitry that processes the electrical signals to generate data about the radiation beam.

The x-ray tube and radiation detector can be components in an x-ray system, such as a computed tomography (CT) system or scanner, which includes a gantry that rotates both the x-ray tube and the detector to generate various images of the object at different angles. The gravitational (G) forces imposed by higher gantry speeds and higher anode rotational speeds used in CT scanners can produce additional stresses on the bearing assembly.

The technology (systems, devices, and methods) described herein provides solutions to reduce the stresses on conventional bearing assemblies in a rotating x-ray system (e.g., CT scanner).

BRIEF DESCRIPTION OF THE DRAWINGS

FIGS. 14A-14B illustrate views of an example anode assembly of an x-ray tube with a sector stator and a lift electromagnet.

DETAILED DESCRIPTION OF SOME EXAMPLE EMBODIMENTS

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Numbers provided in flow charts and processes are provided for clarity in illustrating steps and operations and do not necessarily indicate a particular order or sequence. Unless otherwise defined, the term "or" can refer to a choice of alternatives (e.g., a disjunction operator, or an exclusive or) or a combination of the alternatives (e.g., a conjunction operator, and/or, a logical or, or a Boolean OR).

The invention relates generally to reducing the loading on a bearing assembly of an anode assembly of an x-ray tube using magnetics and, more particularly, to a electromagnet for lifting a shaft of the anode assembly to counter balance a force due to a gantry rotation and gravity in a CT a computed tomography (CT) system. Example embodiments illustrate a lift electromagnet (or magnetic actuator or lift magnet) in various positions relative to the anode and bearing assembly and various variations of the lift electromagnet and component to support magnetic lift on the bearing assembly in the anode assembly. The magnetic lift may also be referred to as a hybrid bearing.

Reference will now be made to the drawings to describe various aspects of example embodiments of the invention. It is to be understood that the drawings are diagrammatic and schematic representations of such example embodiments, and are not limiting of the present invention, nor are they necessarily drawn to scale.

Example X-Ray Tube

Figure 1:
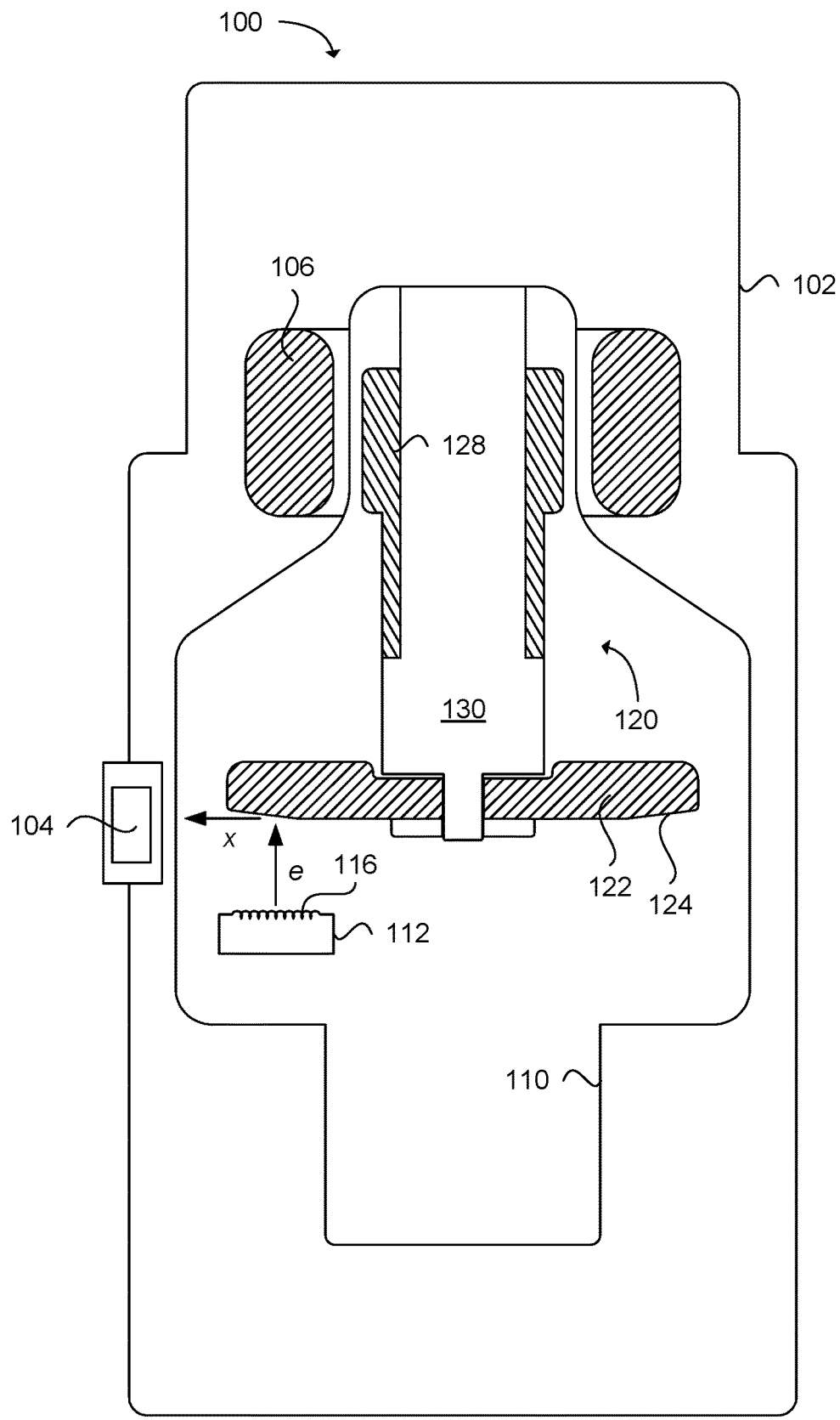
FIG. 1 illustrates a block diagram of an example x-ray tube.

FIG. 1 is a block diagram of an example rotary or rotating anode type x-ray tube 100 with a rotatable disc-shaped anode 122. The x-ray tube 100 includes a housing 102 and an x-ray insert 110 within the housing 102. The housing 102 encloses the insert 110. A coolant or air may fill the space or cavity between the housing 102 and the insert 110. A cathode 112 and an anode assembly 120 are positioned within an evacuated enclosure, also referred to as the insert 110. The anode assembly 120 includes the anode 122, a bearing assembly 130, and a rotor 128 mechanically coupled to the bearing assembly 130. The anode 122 is spaced apart from and oppositely disposed to the cathode 112. The anode 122 and cathode 112 are connected in an electrical circuit that allows for the application of a high voltage potential between the anode 122 and the cathode 112. The cathode 112 includes an electron emitter 116 that is connected to an appropriate power source (not shown).

As disclosed in FIG. 1, prior to operation of the example x-ray tube 100, the insert 110 is evacuated to create a vacuum. The insert 110 encloses the vacuum. Then, during operation of the example x-ray tube 100, an electrical current is passed through the electron emitter 116 of the cathode 112 to cause electrons "e" to be emitted from the cathode 112 by thermionic emission. The application of a high voltage differential between the anode 122 and the cathode 112 then causes the electrons "e" to accelerate from the cathode electron emitter toward a focal spot on a focal track 124 that is positioned on the anode 122. The focal track 124 may be composed for example of tungsten (W) and rhenium (Re) or other materials having a high atomic ("high Z") number. As the electrons "e" accelerate, they gain a substantial amount of kinetic energy, and upon striking the rotating focal track 124 some of this kinetic energy is converted into x-rays "x".

The focal track 124 is oriented so that emitted x-rays "x" are visible to an x-ray tube window 104. The x-ray tube window 104 includes an x-ray transmissive material, such as beryllium (Be), so the x-rays "x" emitted from the focal track 124 pass through the x-ray tube window 104 in order to strike an intended object (not shown) and then the detector to produce an x-ray image (not shown). FIG. 1 illustrates a single window 104 on the housing 102 (e.g., with a glass insert that allows radiation to pass through the glass of the insert). In other examples, a separate window may be included on both the insert 110 (e.g., a metal insert) and the housing 102, or a window may be included on just the insert 110.

As the electrons "e" strike the focal track 124, a significant amount of the kinetic energy of the electrons "e" is transferred to the focal track 124 as heat. To reduce the heat at a specific focal spot on the focal track 124, a disc-shaped anode target is rotated at high speeds, typically using an induction motor that includes a rotor 128 and a stator 106. The induction motor can be an alternating current (AC) electric motor in which the electric current in the rotor 128 needed to produce torque is obtained by electromagnetic induction from a magnetic field of stator winding. Then, the rotor 128 rotates a hub of the bearing assembly 130 that is mechanically coupled to the anode 122, which rotates the anode 122. In another example (not shown), the motor can be a direct current (DC) motor.

X-rays "x" are produced when high-speed electrons 'e" from the cathode 112 are suddenly decelerated by striking the focal track 124 on the anode 122. To avoid overheating anode 122 from the electrons "e", the rotor 128 and sleeves (not shown) rotate the anode 122 and other rotatable components at a high rate of speed (e.g., 80-300 Hz) about a centerline of a center shaft (not shown). The x-ray tube 100 can also include other cooling features to reduce the heat generated by the anode 122 and the cathode 112.

Example Gantry

The x-ray tube and radiation detector can be included in a rotational x-ray system, such as a computerized tomography (CT) scanner. Computerized tomography (CT) involves the imaging of the internal structure of an object by collecting several projection images ("radiographic projections") in a single scan operation ("scan"), and is widely used in the medical field to view the internal structure of selected portions of the human body. Typically, several two-dimensional projections are made of the object, and a three-dimensional representation of the object is constructed from the projections using various tomographic reconstruction methods. From the three-dimensional image, conventional CT slices through the object can be generated. The two-dimensional projections are typically created by transmitting radiation from a "point source" (e.g., x-ray tube) through the object, which will absorb some of the radiation based on its size, density, and atomic composition, and collecting the non-absorbed radiation onto a two-dimensional imaging device (i.e., radiation detector), or imager, which comprises an array of pixel detectors (simply called "pixels"). Such a CT system is shown in FIG. 2.

Figure 2:
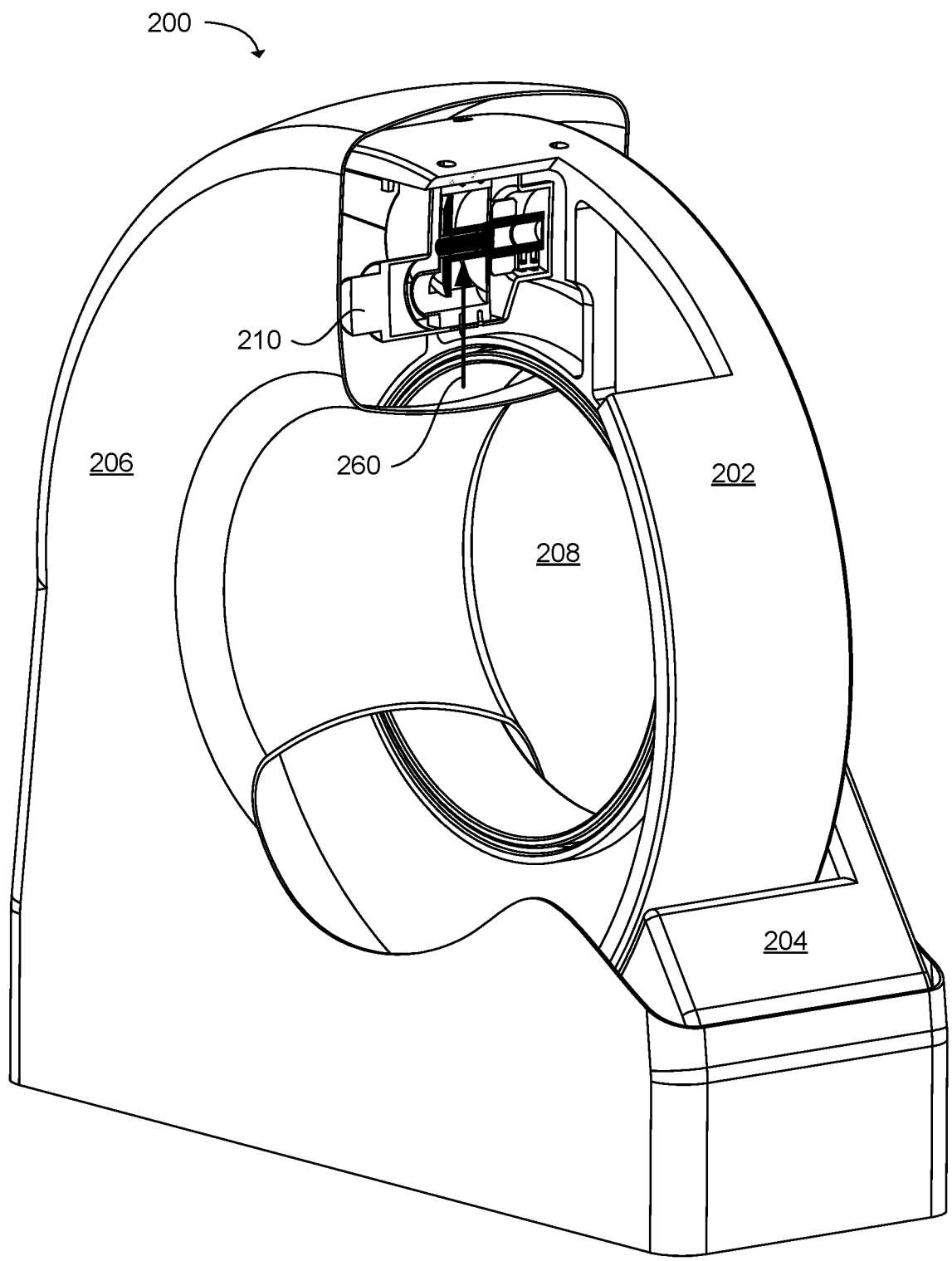
FIG. 2 illustrates a perspective view of a partially exposed example gantry assembly.

FIG. 2 illustrates a rotating assembly (or gantry assembly) 200, or gantry, of a rotating x-ray system. The gantry includes a stationary gantry frame 204 that supports a rotatable gantry frame 202. The rotating gantry can support an x-ray tube 210 and an radiation detector or imager (not shown). The gantry also includes a gantry cover 206 to shield the rotating components and frame from a user as well as provide an aesthetic covering. The rotating gantry frame can include an annular shape (i.e., ring shape) that rotates at a high speed about a center of axis in an gantry aperture 208 of the rotating gantry frame. The centrifugal force 260 (or gantry force) on components disposed on the rotating gantry frame can experience a high force, which can exceed a gravitational force (g-force, G's, g's, or G loads) or a multiple of the g-force (e.g., 20 times the g-force). For example, components on an x-ray tube, such as the bearing assembly, where the x-ray tube is mounted on the rotating gantry frame at a radius of 0.7 meters from the center of axis and the rotating gantry frame is rotating at 0.275 seconds/rotation (sec/rot) can experience a force of 37 gs.

Improvements in CT scanning use higher gantry rotational speeds. As a result, x-ray tube bearing life of conventional bearings is being adversely affected. Higher gantry speeds can lower the acceptable life of the bearing assembly. Liquid metal bearings (LMB) is a technology that can effectively handle higher G loads but implementing LMB can increase cost significantly and require significant changes to the system design. The magnetic lift device described herein can allow for modification to existing system or can provide backwardly compatible life improvements that are very cost effective. As discussed, the gantry force 260 can add additional stress and wear on the components, such as the bearing assembly (250 in FIG. 6) of an anode assembly (240 in FIG. 6) in the x-ray tube 210, as illustrated in FIG. 3.

Figure 3:
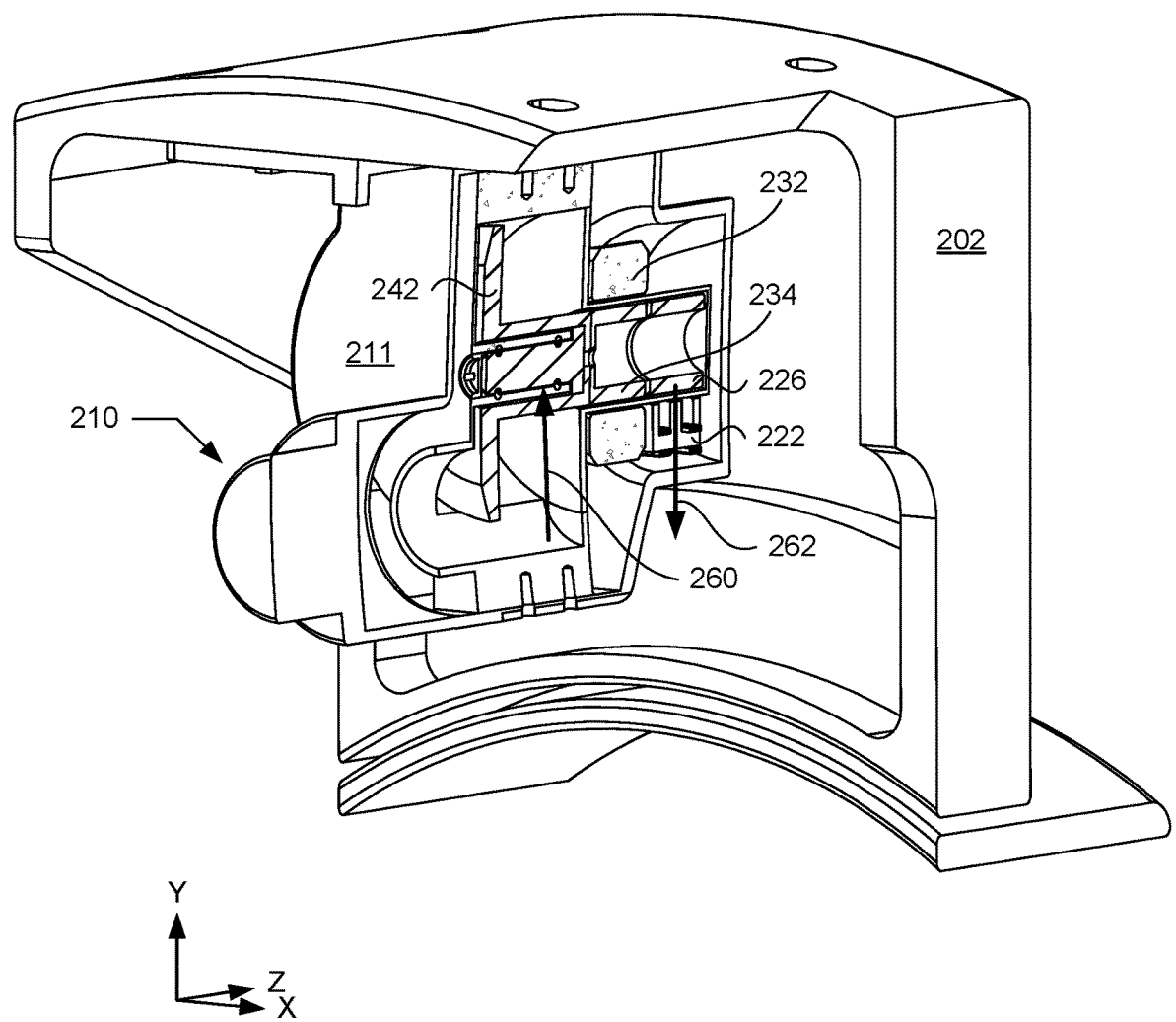
FIG. 3 illustrates a perspective cross section view of an example x-ray tube with a lift electromagnet coupled to a rotating gantry frame.

FIG. 3 illustrates an x-ray tube 210 attached to the rotatable gantry frame 202. The x-ray tube includes a tube housing 211, an anode 242 that can receive electrons emitted by a cathode (112 of FIG. 1), a rotor 234 coupled to a shaft of the anode, a stator 232 surrounding the rotor, a ferromagnetic lift shaft (or lift shaft) 226 coupled to the rotor, and a lift electromagnet 222 (or lift multipole electromagnet or electromagnet) that can provide lift 260 to the lift electromagnet and thereby lifting the rotor and the shaft of the anode along a substantially similar centerline or rotation axis. As used herein, lifting refers to a force along an axis (e.g., a single axis or a substantial radial direction of the ferromagnetic lift shaft). The lifting or lift force can be an attractive force that pulls two components together (e.g., the ferromagnetic lift shaft and the lift electromagnet) or an repulsive force or repelling force that pushes two components apart (e.g., the ferromagnetic lift shaft and the lift electromagnet). Reference will often be made to the lifting or the lift force as an attractive force, but it is understood that the lifting or the lift force can be a force with any magnitude (positive or negative) along the radial axis. For descriptive purposes, FIG. 3 provides a Cartesian coordinate system with the y-axis in the vertical direction, the x-axis in the horizontal direction, and the z-axis orthogonal to the x-y plane. The rotation of the gantry occurs in the x-y plane and the centerline of the shaft of the anode or an axis of rotation of the anode occurs along a z-axis. During rotation, when the x-ray tube is vertical with the axis of gantry rotation, the gantry force applies a force in the vertical direction (i.e., y-axis). The lift electromagnet 222 can apply a magnetic lift force 262 (e.g., magnetic force, counter acting force, or balancing force) in the opposite direction. The magnetic force can offset, dampen, reduce, or balance the forces (including centrifugal force of the gantry) on the bearing assembly or anode assembly. The lift force can reduce vibration or noise, increase bearing life, increase the bearing load capability, control thermal contact, improve the centering and precision of the rotating assembly, and allow the use of smaller bearings (e.g., ball bearings or other rotating bearings) or use other bearing types in a rotating type x-ray tube (e.g., rotating anode type x-ray tube). Reducing vibration and noise can also make the scanning process more pleasant for a patient. Examples are shown with a rotating anode. In other examples (not shown), the cathode rotates while the anode remains stationary (i.e., rotating cathode type x-ray tube). The principles described herein can also apply to rotating cathode type x-ray tube.

Example Lift Electromagnet

Figure 4:
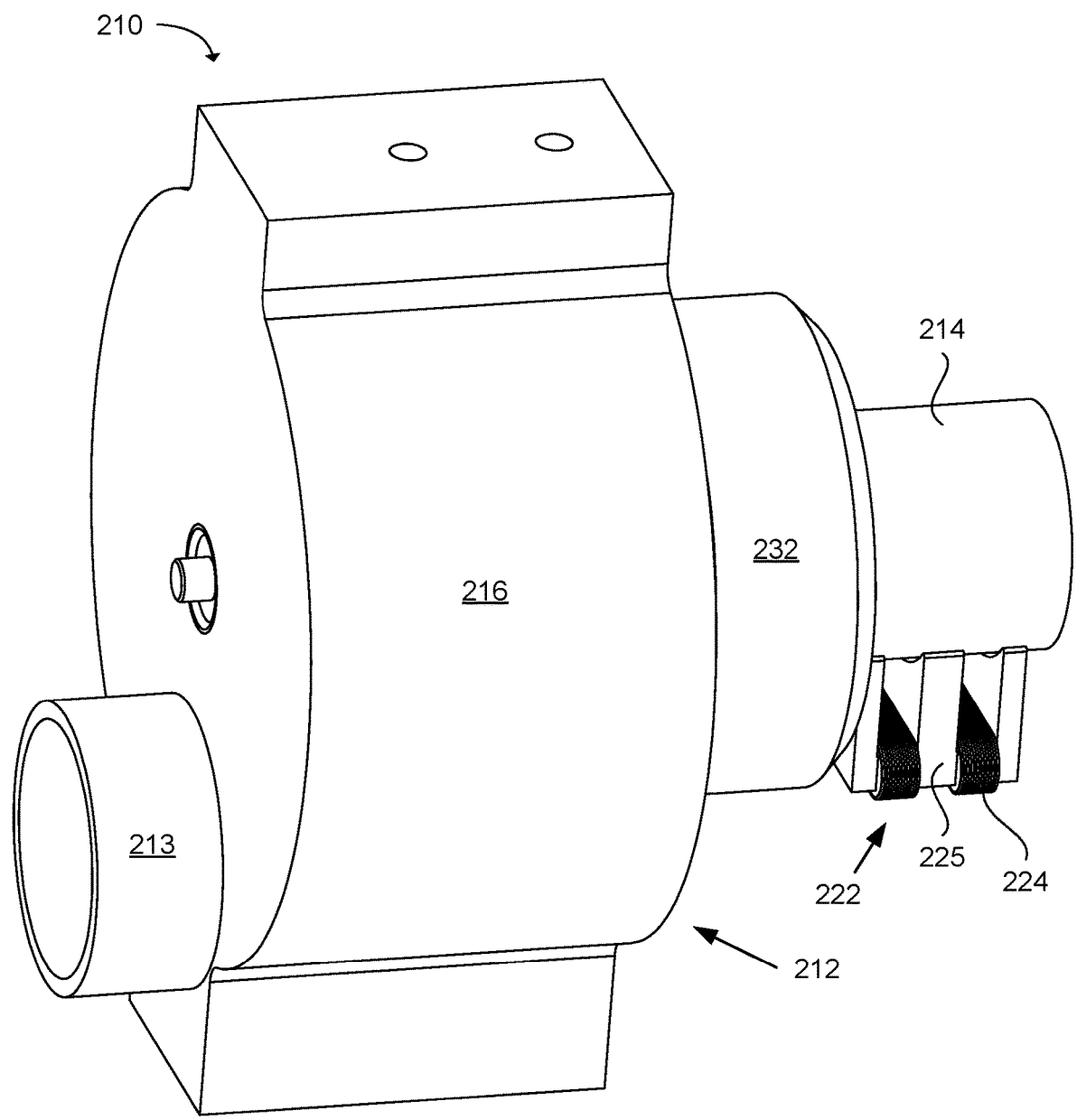
FIG. 4 illustrates a perspective view of an example insert of an x-ray tube.

FIG. 4 illustrates an envelope or insert 212 of an x-ray tube 210. The insert includes a wall (i.e., insert wall or envelope wall) that encloses the cathode and anode in an evacuated chamber or enclosure. The insert wall can enclose a cathode region (not shown), the drift region 213, the anode region 216, the rotor region (215 of FIG. 6), and the lift region 214.

Figure 5:
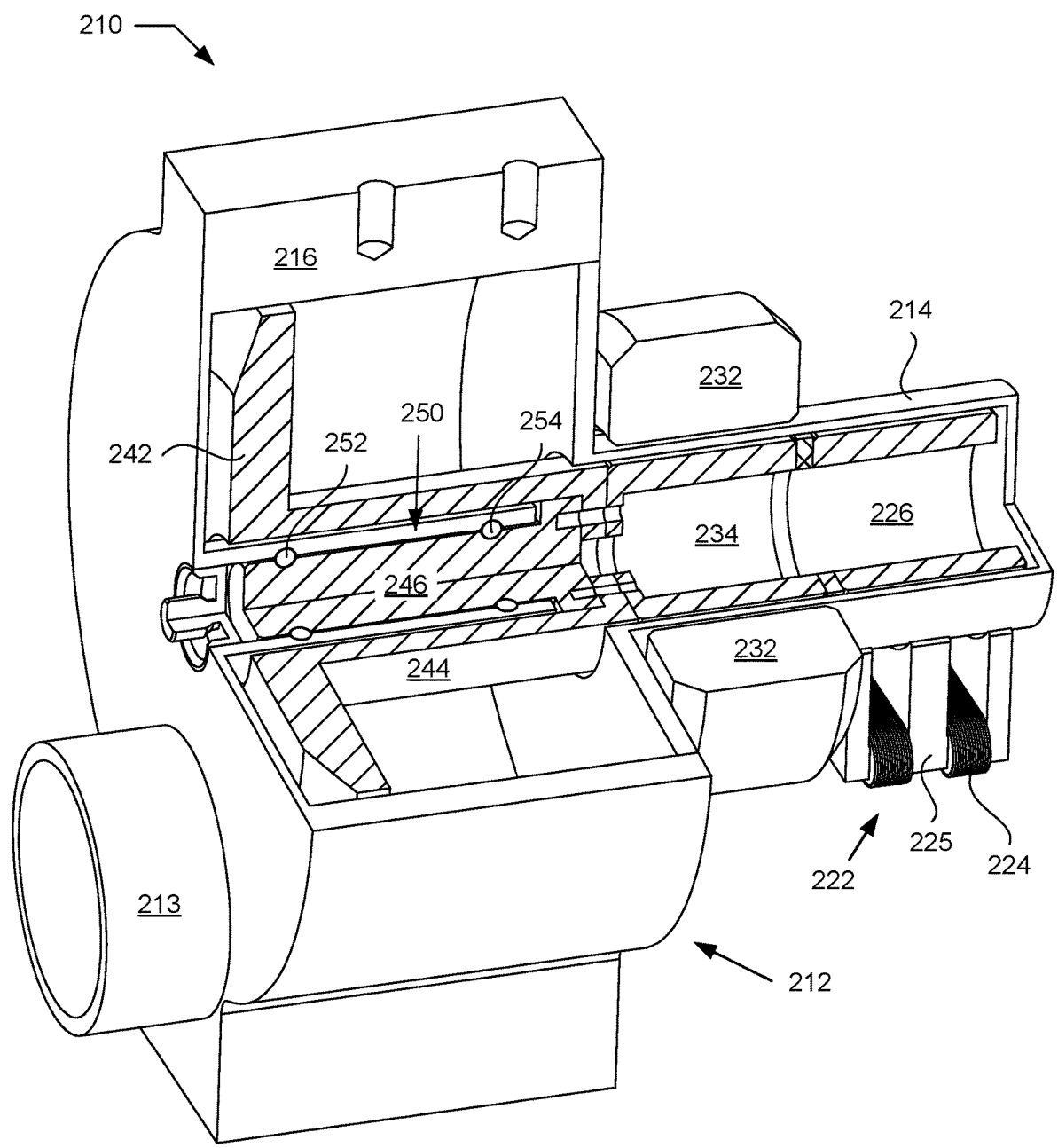
FIG. 5 illustrates a perspective section view of an example insert of an x-ray tube and a lift electromagnet.
Figure 6:
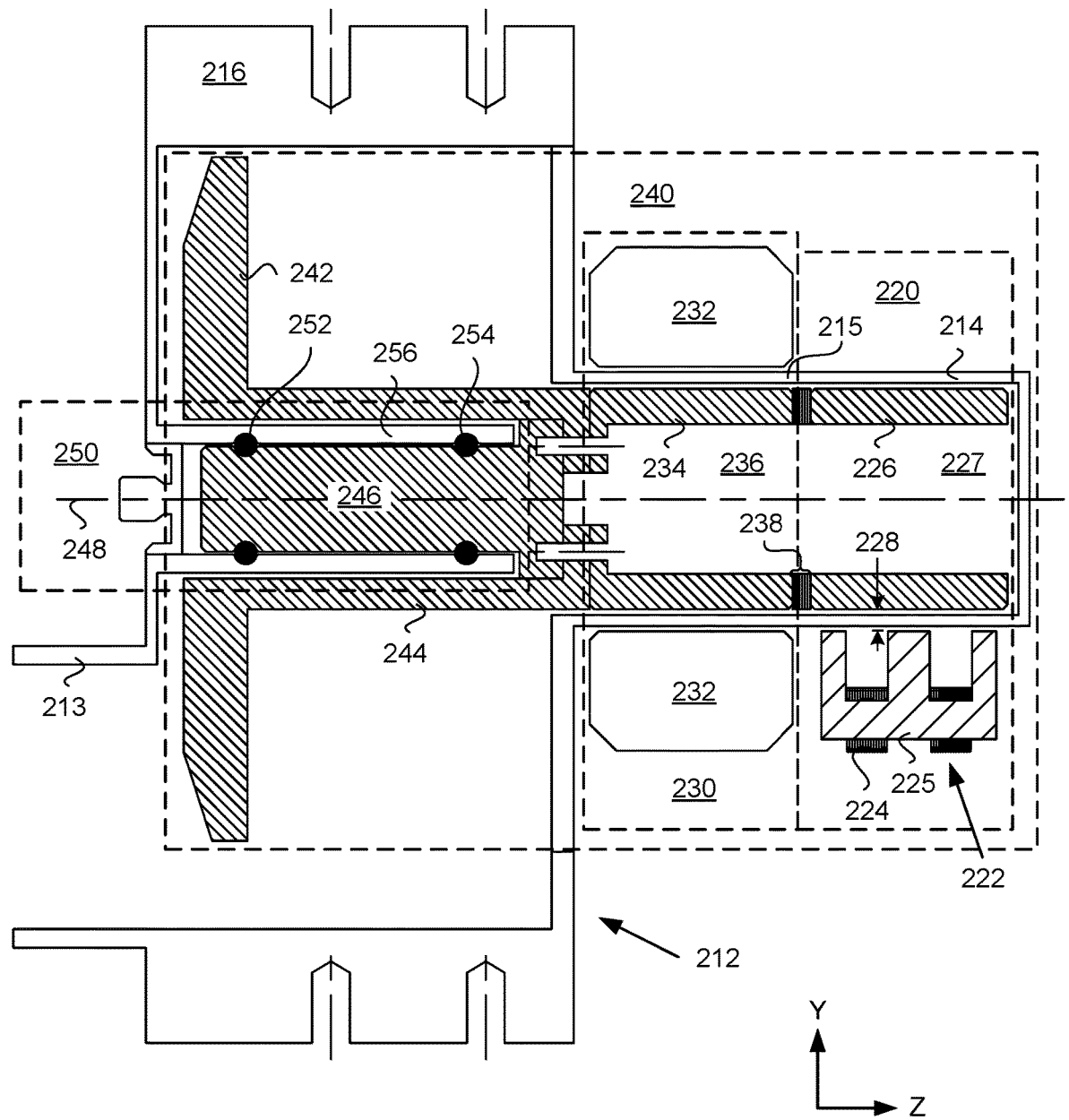
FIG. 6 illustrates a side cross section view of an example anode assembly of an x-ray tube with a lift electromagnet disposed near an end of a rotating shaft.
Figure 7:
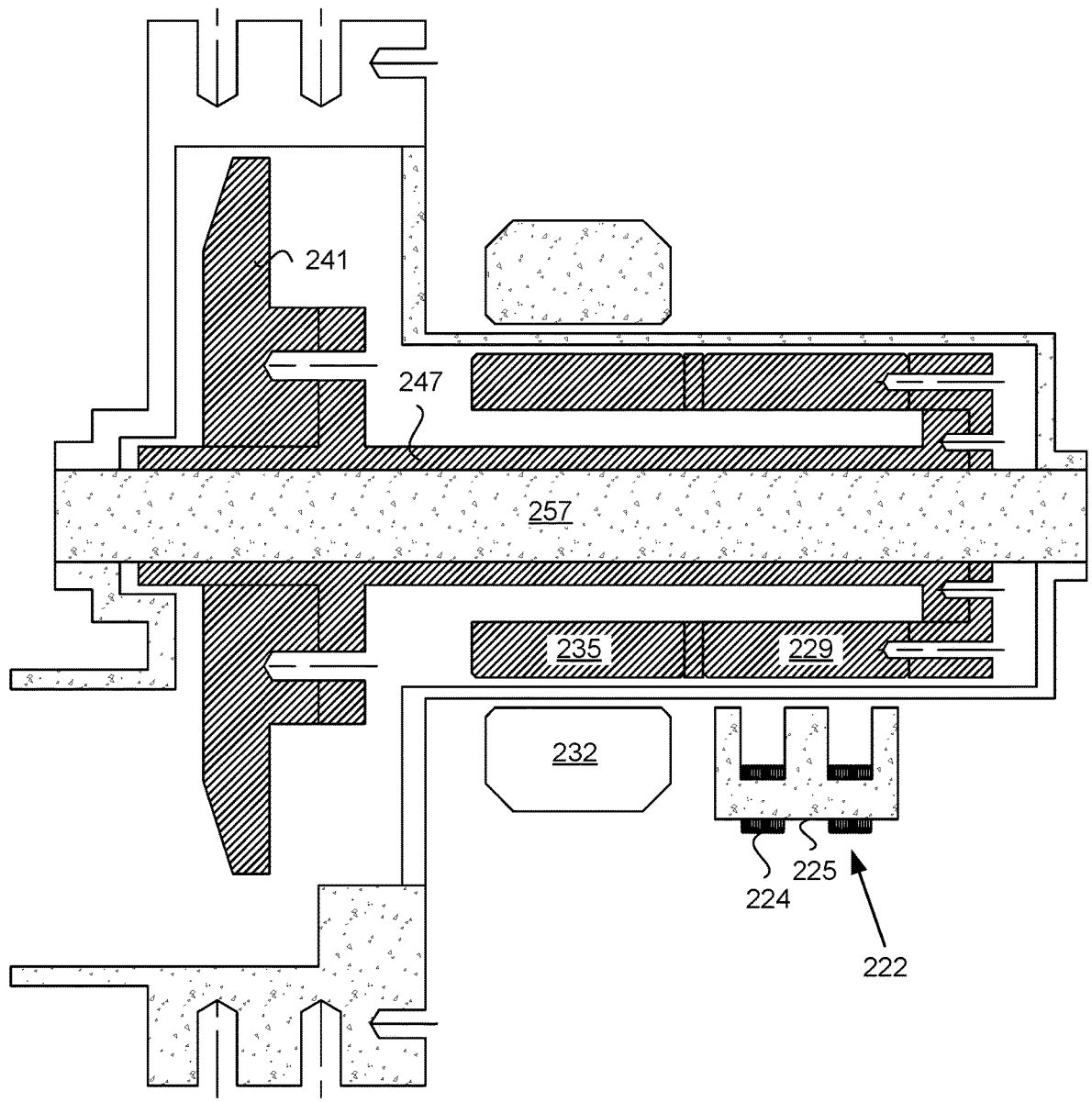
FIG. 7 illustrates a side cross section view of an example anode assembly of an x-ray tube with a lift electromagnet and a plain bearing.

FIGS. 5-6 illustrate various views of an insert 212 of an x-ray tube 210 and a lift electromagnet 222. The x-ray tube includes an anode assembly 240, a bearing assembly 250, a motor assembly 230, and lift assembly 220. The anode assembly, bearing assembly, motor assembly, and lift assembly are designed to rotate about an anode assembly centerline (or bearing centerline) 248. The anode assembly 240 in the anode region includes an anode 242 and an anode outer shaft 244 that supports the anode and an anode inner shaft 246 that is coupled to the outer shaft and rotatably coupled to the bearings (e.g., ball bearings 252 and 254) in the bearing assembly. The inner shaft can include at least one bearing race (e.g., ball bearing race). The bearing assembly 250 includes an outer ball bearing and race 252, inner ball bearing and race 254, and an bearing sleeve 246. Outer refers to a relative position closer to an edge of the anode assembly, closer to the anode, or further away from the motor assembly 230. Inner refers to a position closer to a middle of the anode assembly, further away from the anode, or closer to the motor assembly. Although a roller element bearing type (e.g., tool steel ball bearing or tool steel raceways) is shown, in other embodiments, other bearing types can be used, such as plain bearing (e.g., a sleeve bearing or a journal bearing), as shown in FIG. 7 or hydrodynamic bearings, such as liquid metal bearing (LMB). U.S. patent application Ser. No. 14/968,078, filed Dec. 14, 2015, entitled, "Antiwetting Coating for Liquid Metal," which is incorporated by reference in its entirety, discloses an example of a liquid metal bearing. In FIG. 7, the anode 241 is coupled to an anode shaft or sleeve 247 that acts as the rotating sleeve for the bearing assembly. The lift shaft or sleeve 229 can be coupled to the anode sleeve, and the rotor 235 can be coupled to the lift sleeve. A bearing shaft 257 is the stationary component and the anode sleeve 247 is the rotating component of the sleeve bearing.

Referring back to FIGS. 5-6, the motor assembly 230 includes a stator 232 and a rotor 234. The rotor 234 includes a rotor void 236 or opening on one end, which can be a cylindrical void. The rotor with the rotor void can form a rotor sleeve. The rotor void allows the rotor to be attached to the anode shaft (e.g., the anode inner shaft 246) or aligned with the bearing centerline 248. The components (e.g., the anode shaft and the rotor [or rotor shaft]) can be attached to each other using a permanent or semi-permanent fastening or attachment mechanisms, such as a bolt, a nut, a screw, other threaded fastener, a rivet, a pin, a clip, a clasp, a latch, a clamp, a braze, or a weld. The components can be coupled to each other using screws, bolts, semi-permanent attachment mechanism, or permanent attachment mechanism. A semi-permanent attachment mechanism includes a screw, a bolt, or other mechanism that can be attached or unattached through manipulation of a component of the attachment mechanism. A permanent attachment includes a weld, an adhesive, heat or chemical treatment to combine two component together, which requires more than manipulation of the components to remove the components from each other without damage to the components. Unless otherwise stated, the attachment of components can be provide by the semi-permanent attachment mechanism or the permanent attachment. In another example (not shown), the rotor can be integrated with or permanently attached (e.g., welded or brazed) to the anode shaft. The insert wall around the rotor region 215 can be disposed between the rotor and the stator. The electromagnetic induction from the magnetic field of stator winding can pass through insert wall to the rotor. A small gap between the insert wall and the rotor allows the rotor to rotate without mechanical resistance.

Figure 22:
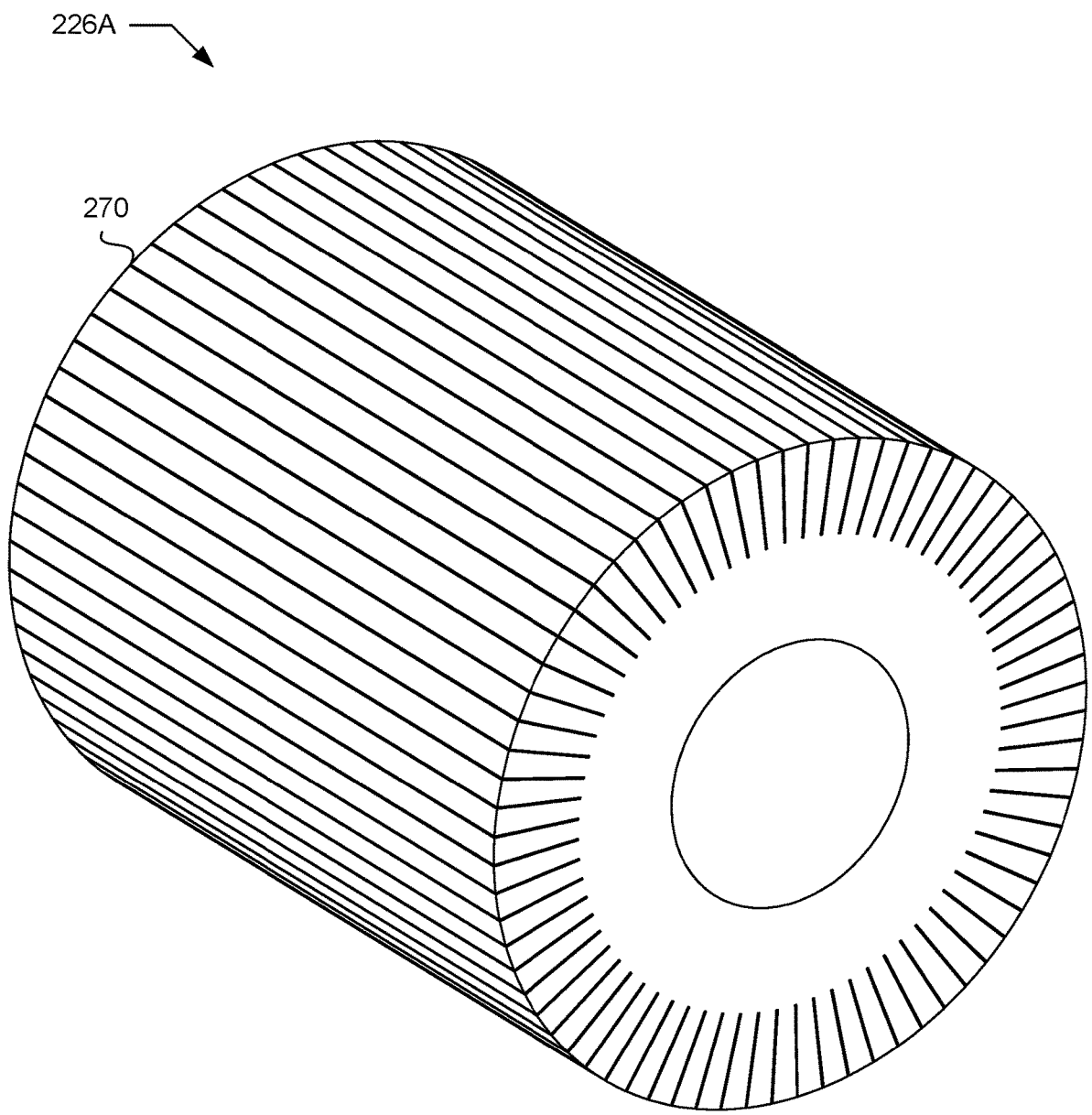
FIG. 22 illustrates a perspective view of an example slotted ferromagnetic shaft.
Figure 23:
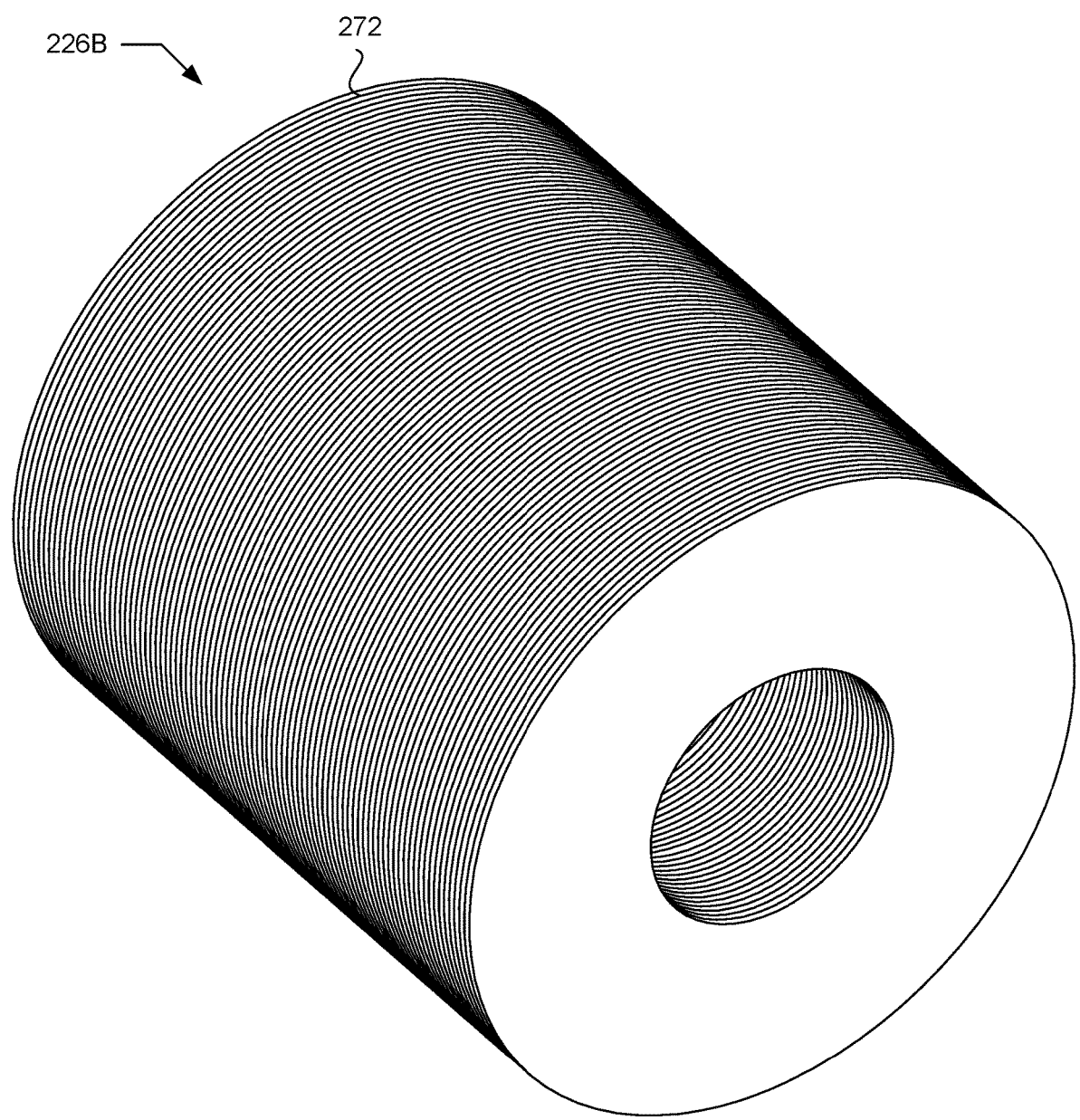
FIG. 23 illustrates a perspective view of an example laminated ferromagnetic shaft.

The lift assembly 220 includes ferromagnetic lift shaft (or lift shaft) 226 coupled to the bearing centerline 248 (e.g., via the rotor) and a lift multiple magnet 222 that can apply a magnetic force on the lift shaft. The lift shaft can include a lift shaft void 227 or opening, which can be a cylindrical void. The lift shaft with the lift shaft void can form a lift sleeve. The lift shaft void allows the rotor to be attached to the rotor or can be aligned with the rotor sleeve or bearing centerline 248. To reduce eddy currents in the shaft, the lift shaft can include slots 270 in the direction of the centerline (z-axis) or laminations 272 in the direction of perpendicular to the centerline (x-y plane). FIG. 22 illustrates a slotted ferromagnetic shaft 226A. FIG. 23 illustrates a laminated ferromagnetic shaft 226B. FIGS. 5-6 illustrates a rotor-to-lift shaft adapter 238 used to couple the rotor to the lift shaft. The rotor-to-lift shaft adapter can include a non-ferromagnetic material to improve magnetic isolation between the rotor assembly and the lift assembly, which both use magnetic fields for operation. In another example (not shown), the lift shaft can be integrated with or permanently attached (e.g., welded or brazed) to the rotor.

The lift multiple magnet includes at least two pole ends that are oriented towards the ferromagnetic shaft. The lift multiple magnet 222 shown in FIGS. 2-6 includes a lift electromagnet core (or core) 225 with three pole ends formed in an "M" or "W" shape with windings 224 wrapped around the core (or core web) between the poles. A tri-pole magnet design, as shown in FIG. 2-6, has the benefit of cancelling eddy currents that can occur as a result of Lenz's law, which reduces heating and increases the magnetic lift force. For maximum lifting force in a three pole configuration, the outer poles can be configured (e.g., by current direction in the windings) to have an opposite polarity as the inner pole (e.g., south pole on the outer poles and north pole on the inner poles; or north pole on the outer poles and south pole on the inner poles). The "M" configuration of the three pole electromagnet can also reduce eddy currents in the magnetic core of the lift electromagnet. In other examples (not shown), additional poles can be used, such as 4 poles, 5 poles, or more poles. For multiple poles, the pole ends oriented towards the ferromagnetic shaft alternate between north and south poles in the direction of the centerline axis (i.e., z-axis).

Eddy currents, also called Foucault currents, are circular electric currents induced within conductors (e.g., metals) by a changing magnetic field in the conductor, due to Faraday's law of induction. Faraday's law of induction is a law of electromagnetism predicting how a magnetic field will interact with an electric circuit to produce an electromotive force (EMF)—a phenomenon called electromagnetic induction. Eddy currents flow in closed loops within electrical conductors, in planes perpendicular to the magnetic field (B-field). The eddy currents can be induced within nearby stationary conductors by a time-varying magnetic field created by an alternating current (AC) electromagnet, for example, or by relative motion between a magnet and a nearby conductor. The magnitude of the eddy current in a given loop is proportional to the strength of the magnetic field (B), the area of the loop, and the rate of change (i.e., frequency) of magnetic flux ($\Phi$), and inversely proportional to the resistivity ($\rho$) of the material.

Material choices can affect the performance of a magnetic device, such as the lift magnet or the ferromagnetic shaft. Magnetic material needs to stay magnetized in vacuum and after processing and be vacuum compatible, such as cold drawn carbon magnetic iron (CMI-C).

The lift magnet or the ferromagnetic shaft include ferromagnetic and ferrimagnetic materials. Ferromagnetic and ferrimagnetic materials are materials that can exhibit spontaneous magnetization. More specifically, a material is "ferromagnetic" if all of its magnetic ions add a positive contribution to the net magnetization. If some of the magnetic ions subtract from the net magnetization (if magnetic ions are partially anti-aligned), then the material is "ferrimagnetic". A ferrimagnetic material is one that has populations of atoms with opposing magnetic moments, as in antiferromagnetism. However, in ferrimagnetic materials, the opposing moments are unequal and a spontaneous magnetization remains. Ferromagnetism occurs in a few substances, such as iron (Fe), nickel (Ni), cobalt (Co), their alloys, and some alloys of rare earth metals. For example, ferromagnetic compounds or materials include manganese bismuth (MnBi), manganese antimony (MnSb), chromium dioxide or chromium(IV) oxide ($CrO_2$), manganese arsenic (MnAs), gadolinium (Gd), dysprosium (Dy), and europium oxide (EuO). Ferrimagnetic compounds or materials include iron (III) oxide ($Fe_2O_3$) or ferric oxide, iron (II,III) oxide ($FeOFe_2O_3$ or $Fe_3O_4$), nickel oxide-iron (III) oxide ($NiOFe_2O_3$), copper oxide-iron (III) oxide ($CuOFe_2O_3$), magnesium oxide-iron (III) oxide ($MgOFe_2O_3$), manganese oxide-iron (III) oxide ($MnOFe_2O_3$), and yttrium iron garnet ($Y_3Fe_5O_{12}$). As used herein and for simplicity in describing the technology, a "ferromagnetic" material refers to a material that can exhibit spontaneous magnetization (i.e., either a ferromagnetic material or a ferrimagnetic material).

The lift magnet or the ferromagnetic shaft can include various materials, such as solid metal core (e.g., a silicon steel core), a powdered metal core (e.g., carbonyl iron core), and ferrite or ceramic cores. The solid metal cores can include "soft" (annealed) iron, "hard" iron, laminated silicon steel, special alloys (specialized alloys for magnetic core applications, such as mu-metal, permalloy, and supermalloy), and vitreous metals (e.g., amorphous metal alloys [e.g. Metglas] that are non-crystalline or glassy).

Laminated silicon steel also referred to as electrical steel, lamination steel, silicon electrical steel, silicon steel, relay steel, or transformer steel, is specialty steel tailored to produce certain magnetic properties, such as a small hysteresis area (i.e., small energy dissipation per cycle or low core loss) and high permeability. The laminated silicon steel material is usually manufactured in the form of cold-rolled strips less than 2 mm thick. These strips are called laminations when stacked together to form a core.

Because the iron in laminated silicon steel is a relatively good conductor, the iron cannot be used in bulk form with a rapidly changing field, as intense eddy currents would appear due to the magnetic field, resulting in huge losses (e.g., induction heating).

Two techniques commonly used together to increase the resistance of iron, and thus reduce the eddy currents, is lamination and alloying of the iron with silicon.

Laminated magnetic cores are made of thin, insulated iron sheets, lying, as much as possible, parallel with the lines of flux. Using this technique, the magnetic core is equivalent to many individual magnetic circuits, each one receiving only a small fraction of the magnetic flux (because their section is a fraction of the whole core section). Because eddy currents flow around lines of flux, the laminations reduce most of the eddy currents from flowing, and restricting any flow to much smaller, thinner and thus higher resistance regions. So, thinner laminations results in lower eddy currents.

Silicon (Si) alloying is also used to increase the resistance of iron (Fe). A small addition of silicon to iron (e.g., around 3%) results in a dramatic increase of the resistivity, up to four times higher than using iron alone. A further increase in silicon concentration impairs the steel's mechanical properties, causing difficulties for rolling due to brittleness.

Among the two types of silicon steel, grain-oriented (GO) and grain non-oriented (GNO), GO is more desirable for magnetic cores. Grain-oriented silicon steel (GOSS) core or a cold-rolled grain-oriented (CRGO) silicon steel is anisotropic, offering better magnetic properties than GNO in one direction. As the magnetic field in inductor and cores is along the same direction, it is an advantage to use grain oriented steel in the preferred orientation. Rotating machines, where the direction of the magnetic field can change, gain no benefit from grain-oriented steel, thus GNO silicon steel can be used.

Ferrites are another type of ferrimagnetic magnetic material that can be used for the lift magnet or the ferromagnetic shaft. A ferrite is a type of ceramic compound typically composed of iron (III) oxide ($Fe_2O_3$) or iron(II,III) oxide ($Fe_3O_4$) combined chemically with one or more additional metallic elements (Me). In another example, a ferrite includes materials that are not composed of iron. Ferromagnetism is a general class of magnetic behavior most commonly associated with iron, but can also be associated with other materials as well. The ferrite is both electrically nonconductive and ferrimagnetic, meaning that the ferrite can be magnetized or attracted to a magnet. Ferrites are usually non-conductive ferrimagnetic ceramic compounds derived from iron oxides such as hematite ($Fe_2O_3$) or magnetite ($Fe_3O_4$) as well as oxides of other metals. Ferrites are, like most of the other ceramics, hard and brittle.

Ferrites can be classified as "soft" or "hard", which refers to the ferrites low or high magnetic coercivity. The magnetic coercivity, coercive field or coercive force, is a measure of the ability of a ferromagnetic material to withstand an external magnetic field without becoming demagnetized. An analogous property, electric coercivity, is the ability of a ferroelectric material to withstand an external electric field without becoming depolarized.

Soft ferrites have a low coercivity and contain nickel (Ni), zinc (Zn), and/or manganese (Mn) compounds, which can be used in electromagnetic cores. The low coercivity means the material's magnetization can easily reverse direction without dissipating much energy (hysteresis losses), while the material's high resistivity prevents eddy currents in the core, which is another source of energy loss. Some examples of soft ferrites include manganese-zinc ferrites (MnZn, with the formula $Mn_aZn_{(1-a)}Fe_2O_4$) and nickel-zinc ferrites (NiZn, with the formula $Ni_aZn_{(1-a)}Fe_2O_4$).

In contrast to soft ferrites, permanent ferrite magnets are made of hard ferrites, which have a high coercivity and high remanence after magnetization. Iron oxide and barium or strontium carbonate are used in manufacturing of hard ferrite magnets. The high coercivity means the materials are very resistant to becoming demagnetized, an essential characteristic for a permanent magnet. They also have high magnetic permeability. Examples of hard ferrites include strontium ferrite ($SrFe_{12}O_{19}$ or $SrO.6(Fe_2O_3)$), barium ferrite, $BaFe_{12}O_{19}$ ($BaO.6(Fe_2O_3)$), and cobalt ferrite ($CoFe_2O_4$ ($CoO.Fe_2O_3$).

Referring back to FIGS. 5-6, the windings (or coils or wires) 224 around the core 225 can include an electrical conductive material (e.g., copper or aluminum) with an electrically insulated sheath, such enameled magnet wire (i.e., transformer wire).

A lift gap 228 is the spacing between the lift shaft 226 and the lift electromagnet 222. The lift gap can include the insert wall in the lift region 214 along with a vacuum between the insert wall and the lift shaft. In some examples, the lift gap includes the space between the insert wall and the lift electromagnet when the lift electromagnet does not touch the insert wall, such as when the lift electromagnet and the insert wall have different electrical potentials. The lift gap that includes the vacuum provides clearance and tolerance for the lift shaft to rotate without mechanical resistance (e.g., friction from touching the insert wall or lift electromagnet). A vacuum and air have a low magnetic permeability (represented by which can reduce the magnetic force from the lift electromagnet applied to the lift shaft. Magnetic permeability is the measure of a material's ability to support the formation of a magnetic field within itself. Reducing the lift gap can strengthen the magnetic force applied to the lift shaft. The force of the lift magnet on the lift shaft is inversely proportional to the square of the lift gap, which force F can be approximated by $$F = \frac{1}{gap^2},$$

where the lift gap is represented by gap. In an example, the lift gap can be less than 2 millimeters (mm). In another example, the lift gap can be less than 1 mm. For the magnetic flux of the magnetic field to primarily act on the lift shaft instead of between poles, the distance between pole ends may be at least ten times greater than the lift gap. In an example the insert wall in the lift region can be less than 1 mm. In another example, the insert wall in the lift region can be less than 0.8 mm. The insert wall in the lift region can use materials with a low magnetic permeability or minimal ferromagnetic properties, such as stainless steel. Gap reducing materials, such as ferrofluids, may also be used in non-evacuated regions.

Figure 8:
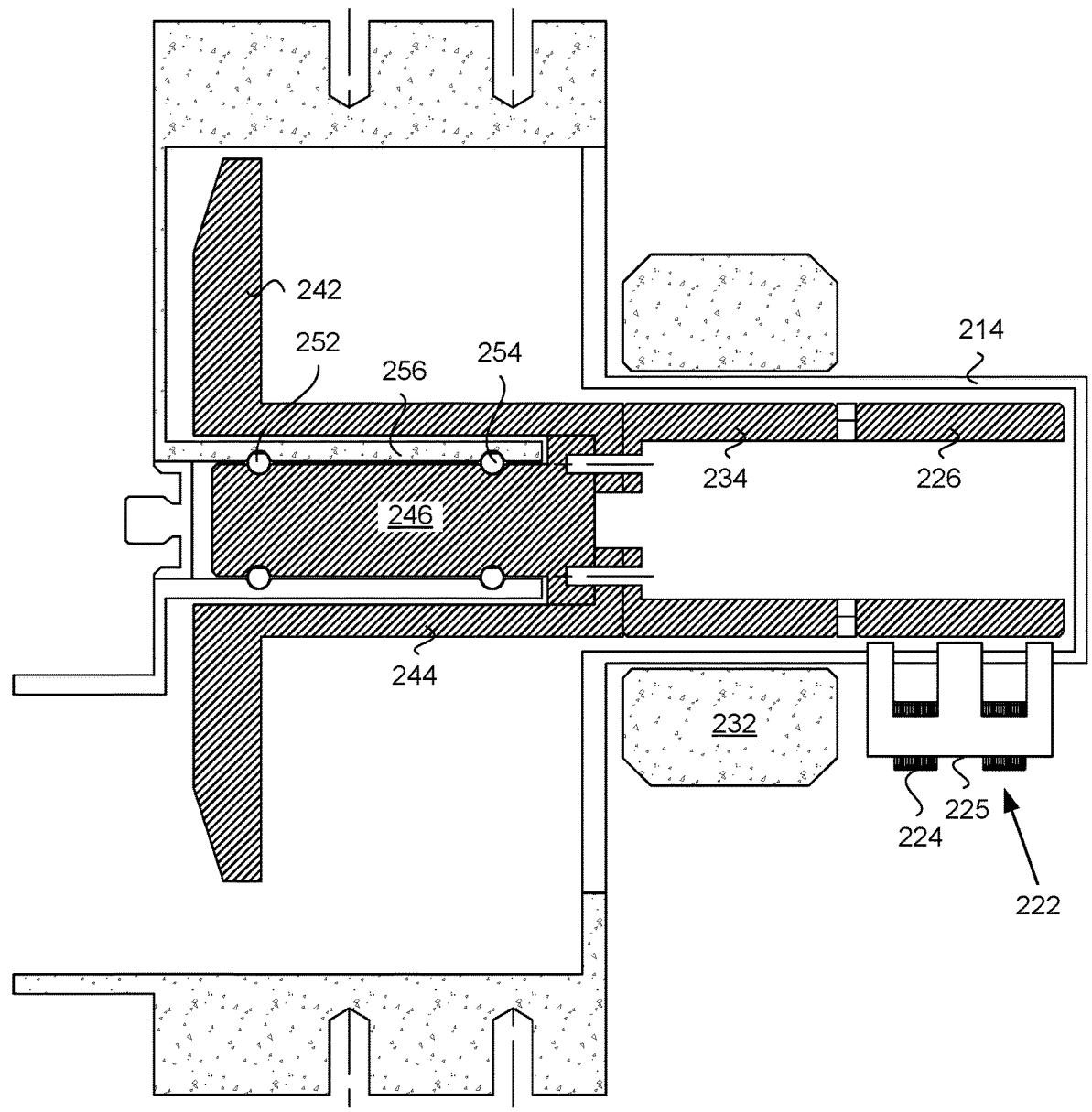
FIG. 8 illustrates a side cross section view of an example anode assembly of an x-ray tube with pole ends of a lift electromagnet disposed in an insert wall.
Figure 9:
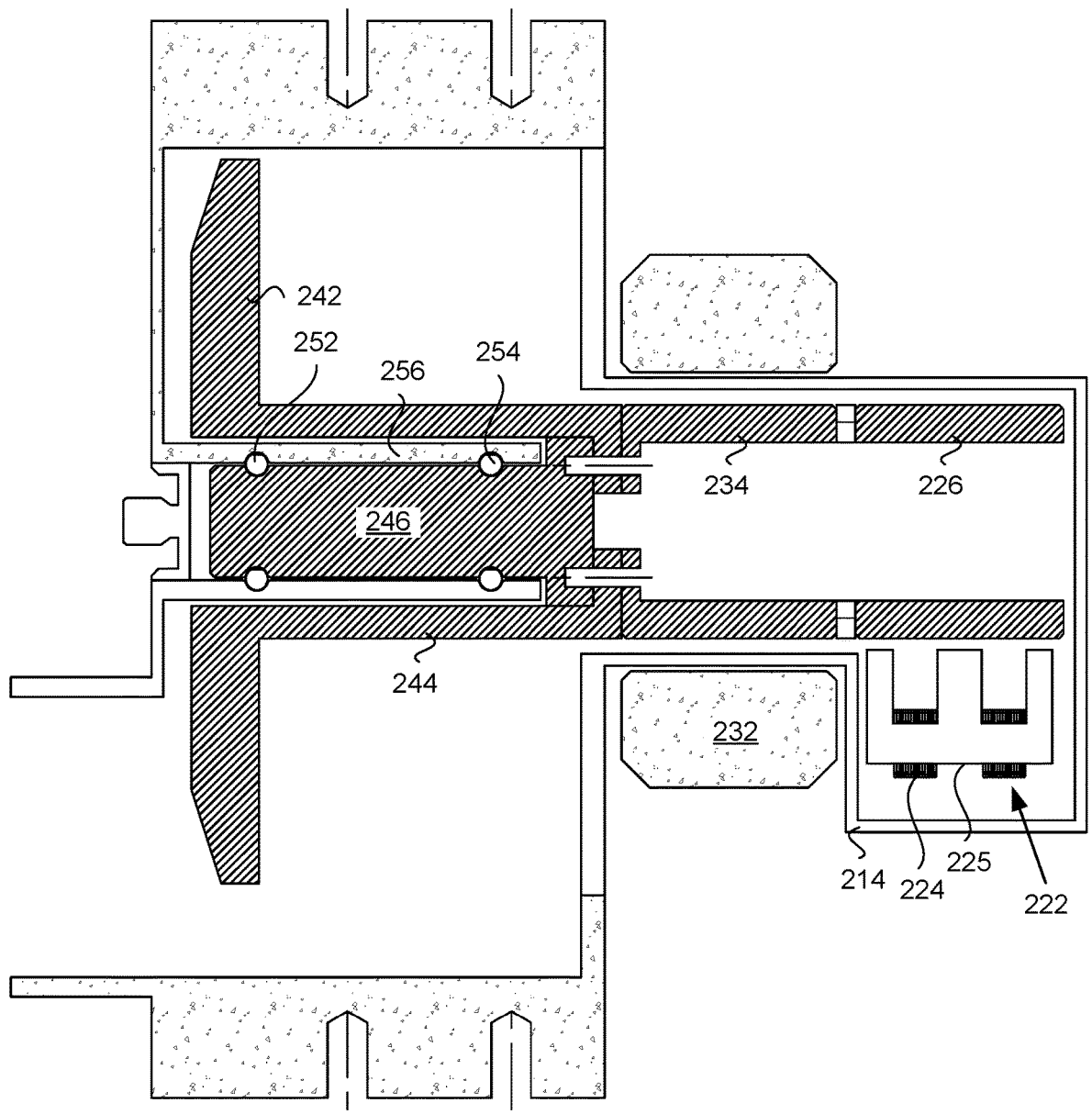
FIG. 9 illustrates a side cross section view of an example anode assembly of an x-ray tube with a lift electromagnet disposed within an insert.

FIG. 8 illustrates pole ends of a lift electromagnet 222 integrated into insert wall 214, which can reduce the lift gap and increase the strength of the magnetic field. The integration of the lift electromagnet into the insert wall can be performed to still maintain the vacuum of the insert. FIG. 9 illustrates a lift electromagnet 222 positioned within the insert 214, which can reduce the lift gap and increase the strength of the magnetic field, but may challenges with dissipating heat from the windings 224 or the core 225 of the lift electromagnet.

The lift electromagnetic 222 apply a magnetic lift force 262 on the rotating assembly (via the lift shaft 226), which can improve bearing life or increase the load bearing capability of the bearing. The magnetic forces of the electromagnet can be used to counteract loads on the bearing assembly, such as the centrifugal force of the gantry, as well as to dampen vibration and add stability to the anode assembly (or rotating assembly) of the x-ray tube. The forces generated by the lift magnet may be applied anywhere on the rotating assembly including at the center or mass (or not at the center of mass) and may employ one or a combination of magnetic lift devices that provide the forces.

Figure 10:
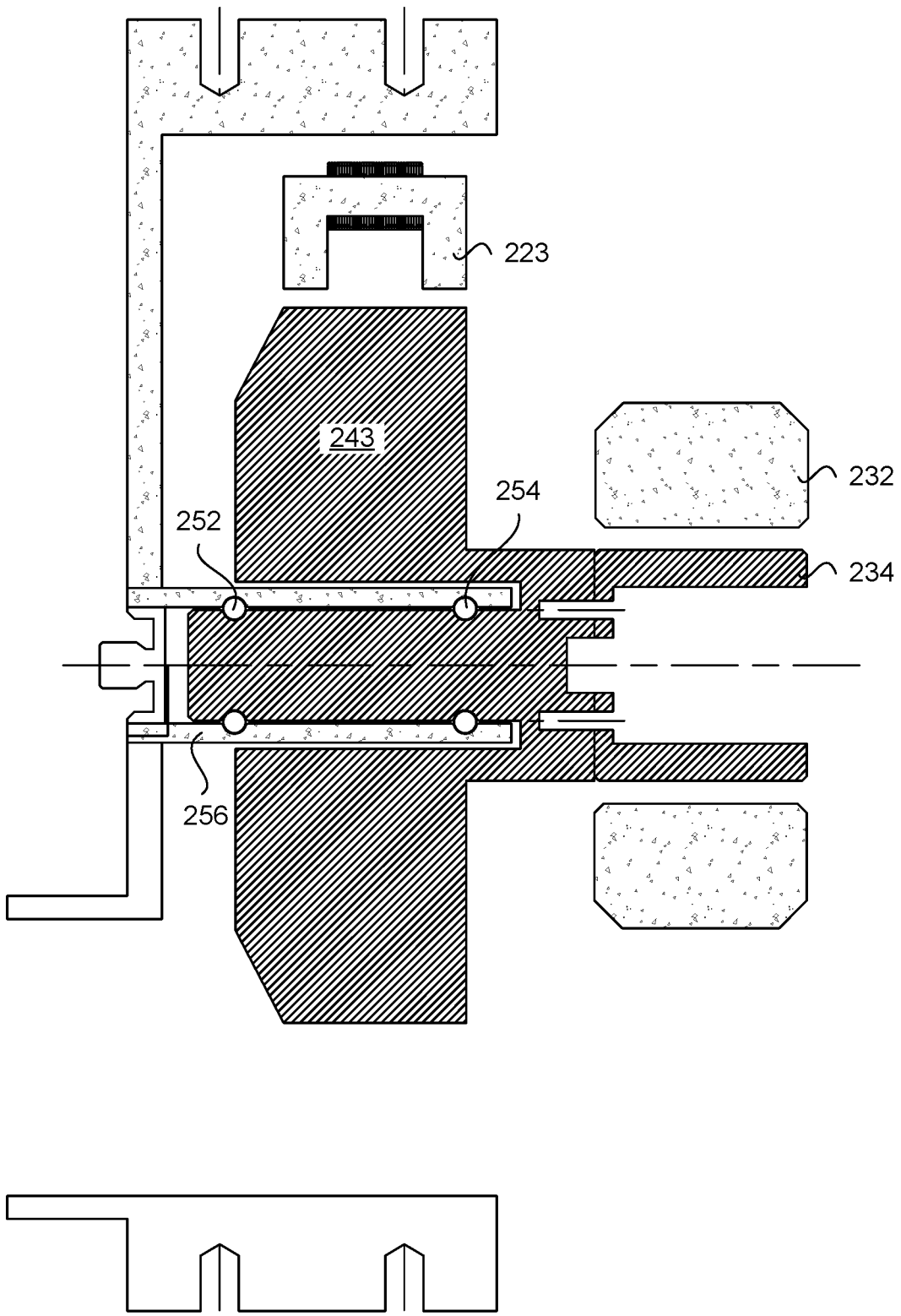
FIG. 10 illustrates a side cross section view of an example anode assembly of an x-ray tube with a lift electromagnet disposed near an anode.

For example, FIG. 10 illustrates a two pole lift electromagnet 223 configured to apply a magnetic force to an anode 243 that also act as a lift shaft. The anode may include materials with a high atomic number (e.g., W and Re) to generate x-rays along with ferromagnetic materials that can be used for magnetic lift on the anode. As illustrated, the lift electromagnet is between two ball bearings and raceways 252 and 254.

Figure 11:
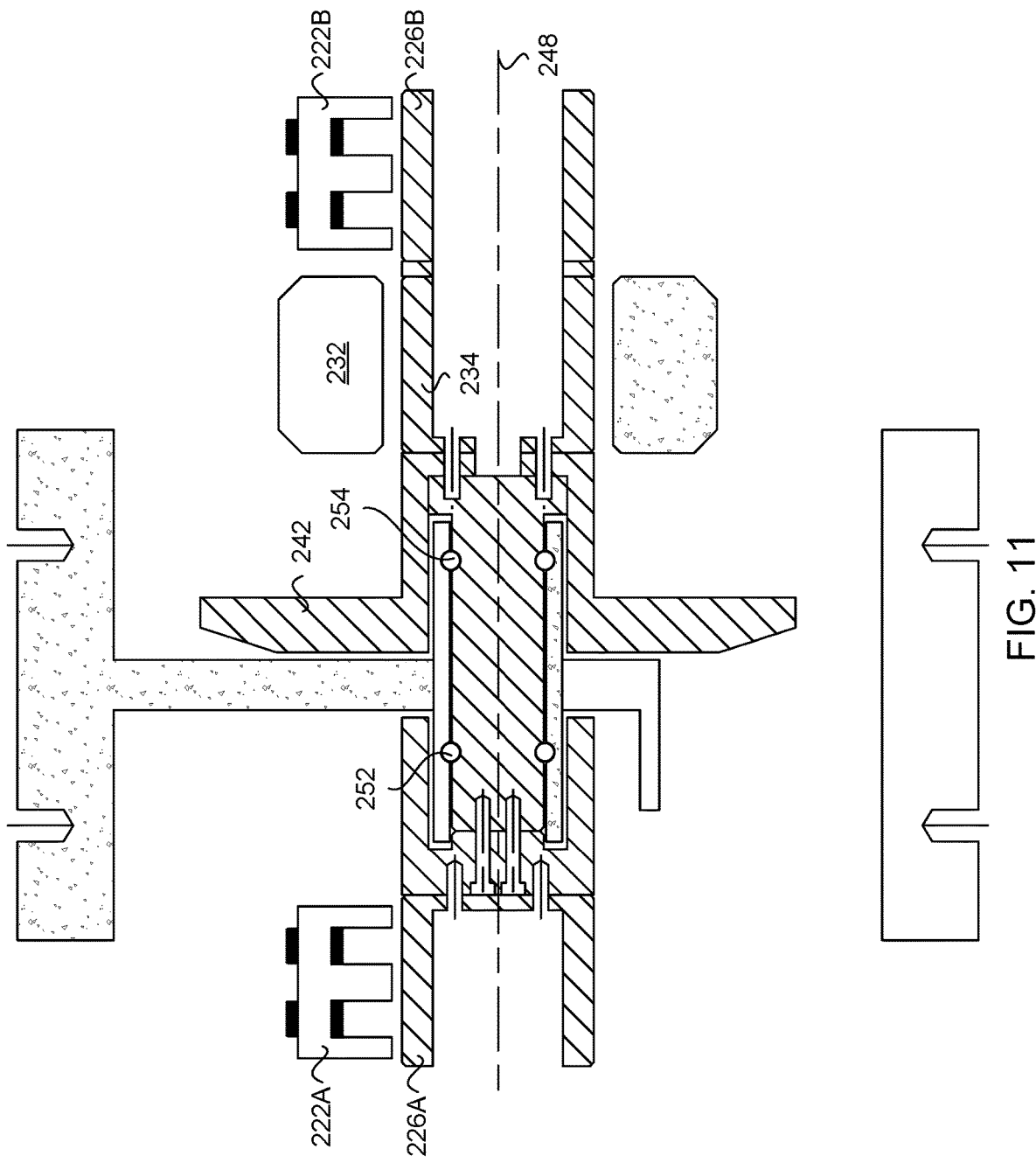
FIG. 11 illustrates a side cross section view of an example anode assembly of an x-ray tube with two lift electromagnets disposed on both sides of an anode.

FIG. 11 illustrates two lift electromagnets 222A-B on opposite ends of an anode centerline 248, which apply force to two different lift shafts or sleeves 226A-B. A first lift shaft 226A is coupled to an anode shaft and a second lift shaft 226B is coupled to the rotor 234. Other positions of the lift electromagnets and lift shaft may also be used relative to the bearing assembly and anode.

Using a magnetic force somewhere along the rotating assembly or at multiple locations on the rotating assembly can reduce the forces on the bearing assembly and improving bearing life. The force may be applied substantially near the center of mass (see FIG. 10), as multiple forces on either side of the center of mass (see FIG. 11) or in a combination of locations along the rotating assembly, such as a cantilevered force (see FIGS. 2-9), or combinations of these approaches.

Figure 12B:
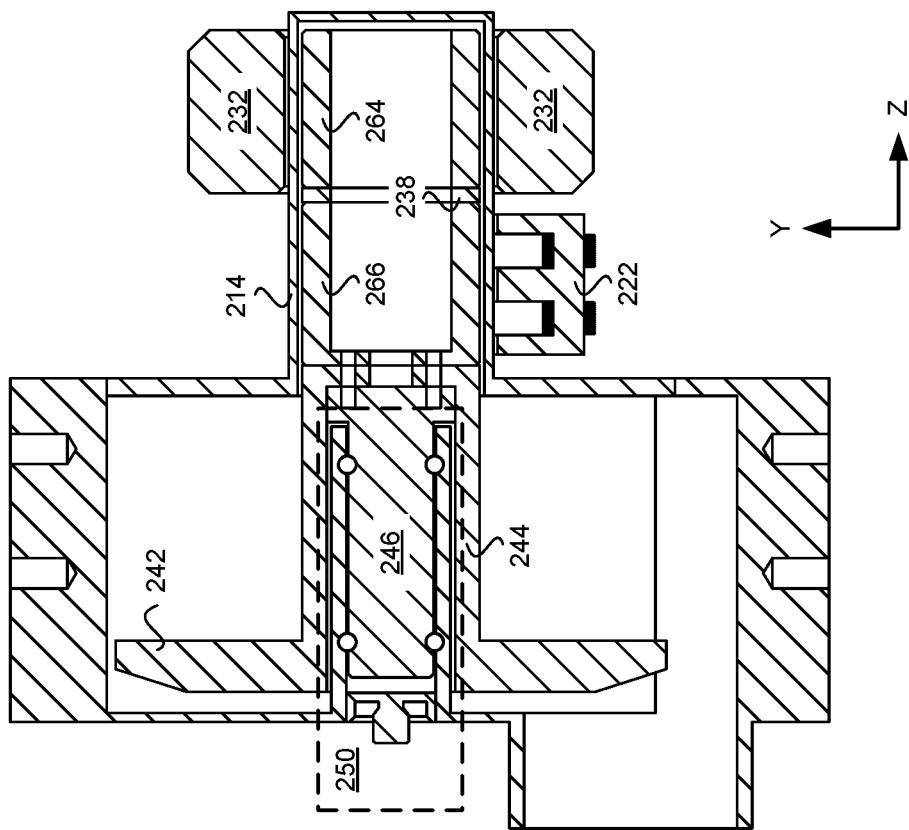
FIGS. 12A-12B illustrate views of an example anode assembly of an x-ray tube with a lift electromagnet positioned between a bearing assembly and a stator.
Figure 12A:
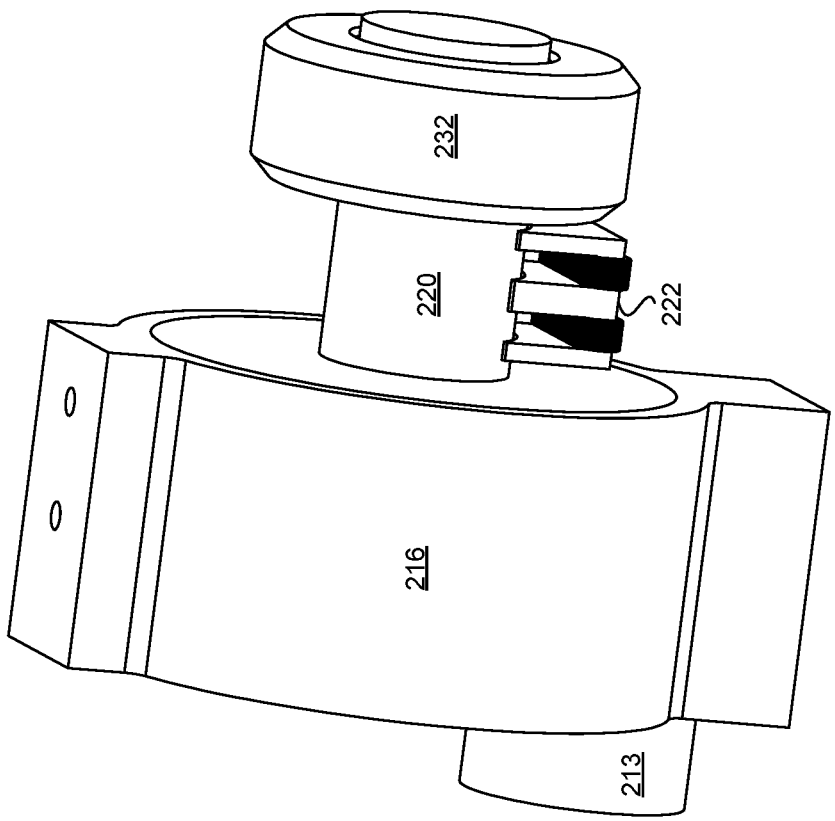

FIG. 12A illustrates a perspective view of an anode assembly of an x-ray tube with a lift electromagnet positioned between a bearing assembly and a stator, and FIG. 12B illustrates a side cross section view of FIG. 12A. The lift magnet is closer to the bearing assembly 250 by switching the position of the stator and lift magnet relative to FIGS. 4-6. The lift electromagnet 222 is configured to lift the lift shaft 266, and the stator 232 is configured to rotate the rotator 264. Many tube housing designs provide a greater internal diameters in the center of the housing (e.g., in anode region). Positioning the lift magnet near the bearing assembly can allow the lift electromagnet 222 to have more coils around the core web 224 (FIG. 6) for the same size core (e.g., length along the z-axis) without changing the tube housing design which can increase the number of turns and force of the lift electromagnet. The lift electromagnet can be used to lower and balance the gantry load reaction forces on the bearing races. Due to the smaller moment arm (i.e., leverage) between the lift force relative to the center of gravity, the input power to the coils may be higher relative to the design in FIGS. 4-6. However, with more turns of the windings around the core web, the lift electromagnet in FIGS. 12A-12B may still have a maximum force greater than the design in FIGS. 4-6 (even with the smaller moment arm).

Figure 13B:
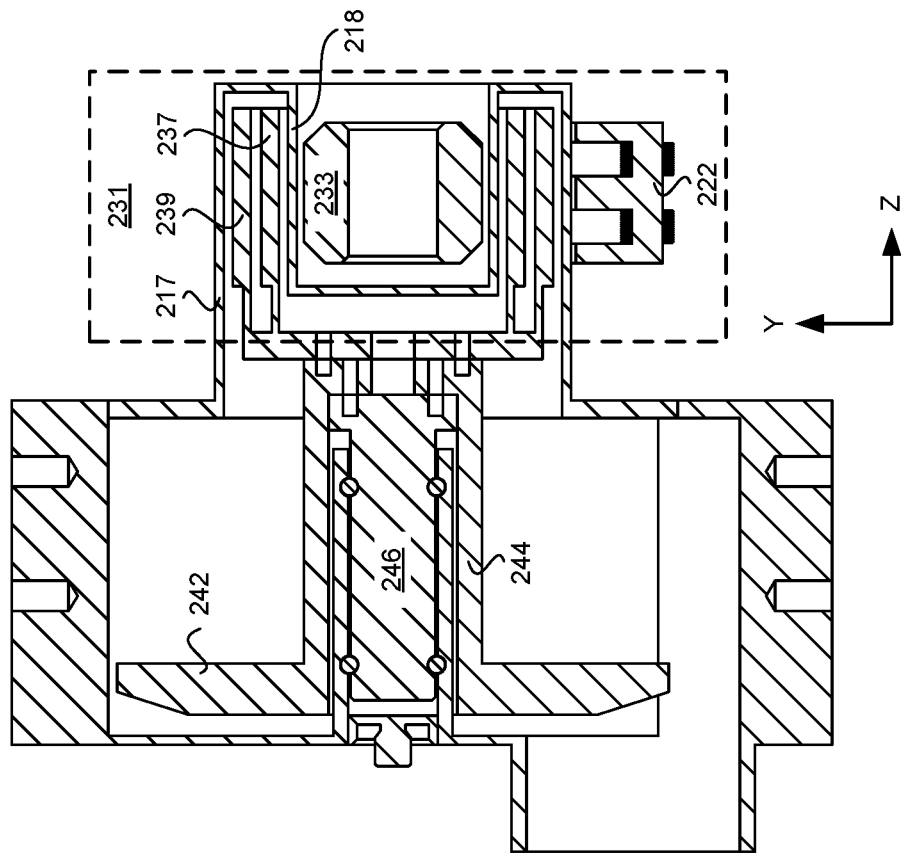
FIGS. 13A-13B illustrate views of an example anode assembly of an x-ray tube with a stator co-planar with a lift electromagnet and the stator is positioned outside the evacuated enclosure.
Figure 13A:
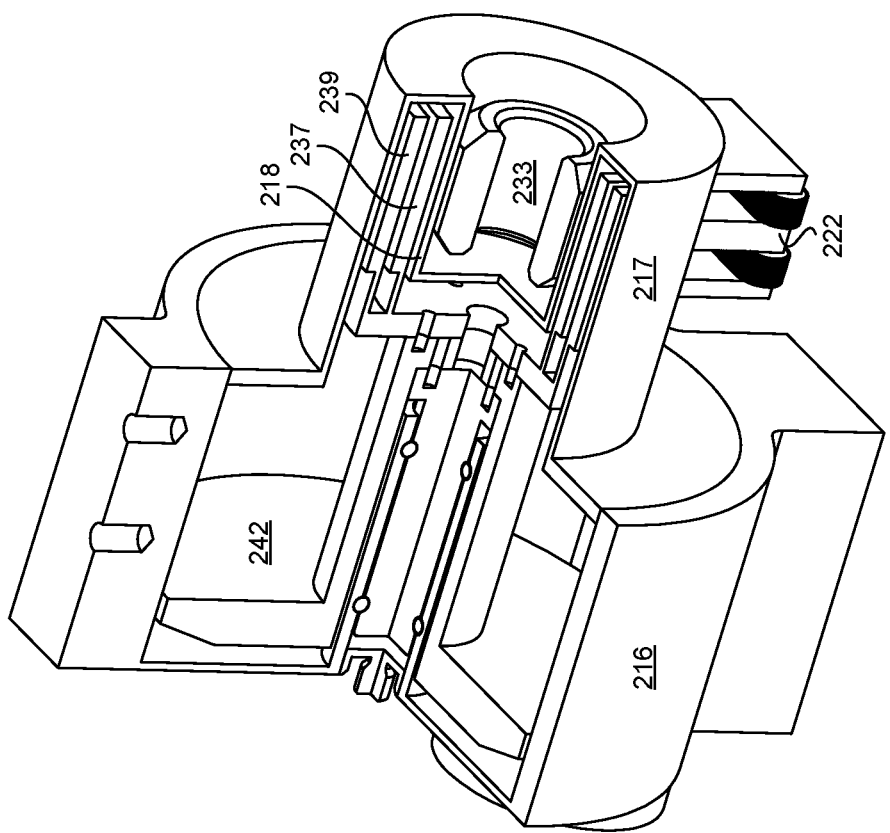

FIG. 13A illustrates a perspective view of an anode assembly of an x-ray tube with a stator 233 co-planar with a lift electromagnet 222, and FIG. 13B illustrates a side cross section view of FIG. 13A. The stator and the lift electromagnet can operate on the same section (i.e., in the same x-y plane along the z-axis) of the rotating shaft. The lift electromagnet and a lift shaft 239 are positioned on the exterior of the motor and lift assembly 231 and the stator and a rotor 237 are positioned on the interior of the motor and lift assembly with the stator positioned in the rotor void. The lift shaft and rotor are coupled together on one end near the bearing assembly. The lift electromagnet and stator can still be positioned outside the evacuated enclosure, where the insert wall 217 around the lift region is positioned between the lift electromagnet and the lift shaft, and the insert wall 218 around the rotor region is positioned between the stator and the rotor. The design shown in FIGS. 13A-13B can reduce the length of the x-ray tube profile (e.g., tube housing and insert along the z-axis) but may increase the diameter of the x-ray tube profile in the motor and lift assembly region.

FIG. 14A illustrates a perspective view of an anode assembly of an x-ray tube with a sector stator 296 co-planar with a lift electromagnet 291 that is configured to act on the same rotor 294 in a motor and lift assembly 290, and FIG. 14B illustrates a side cross section view of FIG. 14A. The lift electromagnet can be similarly configured to lift electromagnets in other design with a lift electromagnet coils 292 wrapped around the lift electromagnet core 293, but with a wedged-shape or pie-shape for the pole ends. In addition, the pole ends can include flanges near the rotor. Although not shown, an insert wall can exist between the sector stator or the lift electromagnet and the rotor. The rotor can function as the lift shaft for the lift electromagnet. A sector stator is a stator that partially surrounds (or partially magnetically couples with) the rotor (e.g., less than 360° of the circumference of the rotor). Similar to a conventional stator, the sector stator has stator coils 297 that are wrapped around or through a stator core 298. In contrast, a conventional stator has symmetrical windings that completely surrounds the rotor over the 360° circumference. In an example, the sector stator covers a sector between 90° and 355°. In another example, the sector stator covers a sector between 180° and 350°. In another example, the sector stator covers a sector between 240° and 330°. The sector stator may have similar functionality to a conventional stator such as similar time to reach a maximum speed, similar size, and similar coil heating. Typically the conventional stator is used to provide the greatest magnetic coupling with the rotor for the smallest stator or rotor design (e.g., fewer coils or less current in the coils). The lift electromagnet may occupy the resulting gap created by the sector stator. In an example, the lift electromagnet covers a sector between 180° and 5°. In another example, the lift electromagnet covers a sector between 120° and 30°. The sector stator 291 shown in FIGS. 14A-14B has a sector of approximately 270° and the lift electromagnet has a sector of less than 90°. The sector stator design may have the same x-ray tube profile as a conventional stator design but with electromagnet lift capability.

Figure 15:
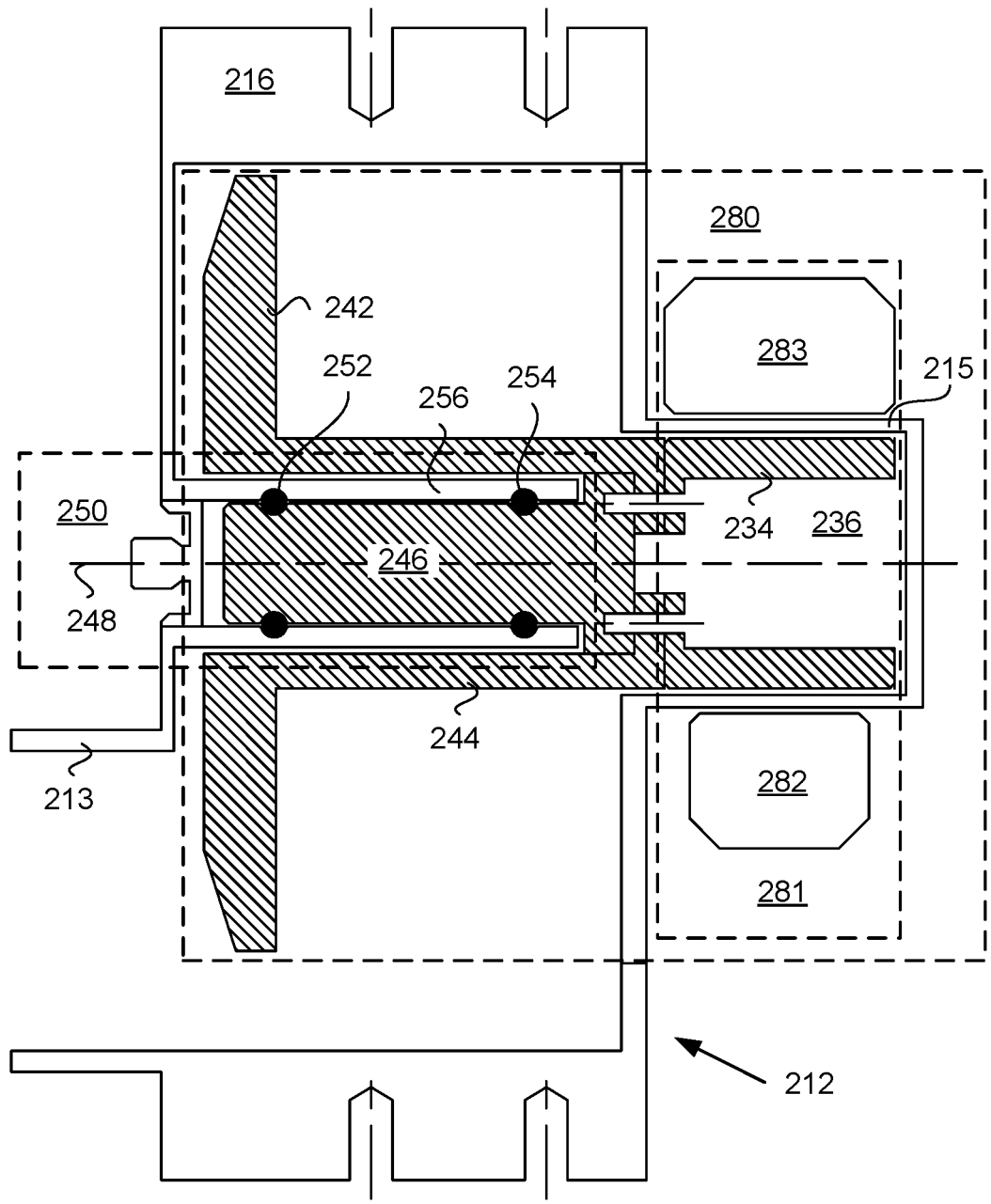
FIG. 15 illustrates a side cross section view of an example anode assembly of an x-ray tube with lift electromagnet combined with a stator.

FIG. 15 illustrates a side cross section view of an anode assembly 280 with a hybrid stator 283 of a motor and lift assembly 281 that combines a lift electromagnet with a convention stator. The stator includes coils that are wound for both lifting (e.g., lift electromagnet) and rotation (e.g., conventional stator). More turns on one part of the stator 283 around each of the poles of the stator can allows the stator to lift as well as drive the rotation while the other parts of the stator 282 can have the conventional number of turns (e.g., less turns than the stator 283). As a result, the stator 283 may be larger to the additional turns (or coils) than the stator 282 configured just for rotation. The coils for rotation (e.g., coils for AC) can be separate from the coils for lift (e.g., coils for AC). For example, the stator can contain additional windings that allow a DC magnetic field to be superimposed over the rotating AC field so the stator lifts as well as rotates. The rotor can function as the lift shaft as well as the convention rotor.

Figure 16B:
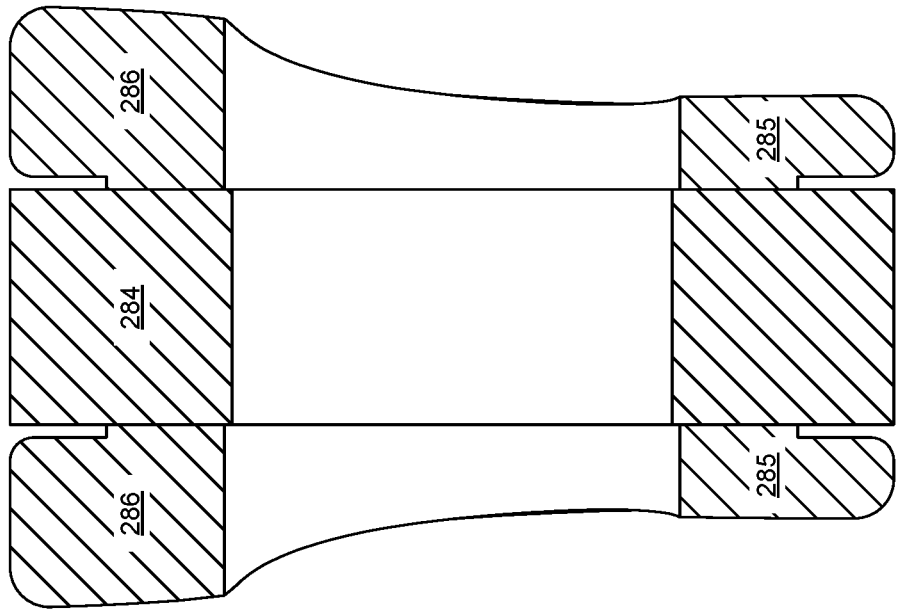
FIGS. 16A-16B illustrate views of an example stator with coils of a lift electromagnet integrated with stator coils.
Figure 16A:
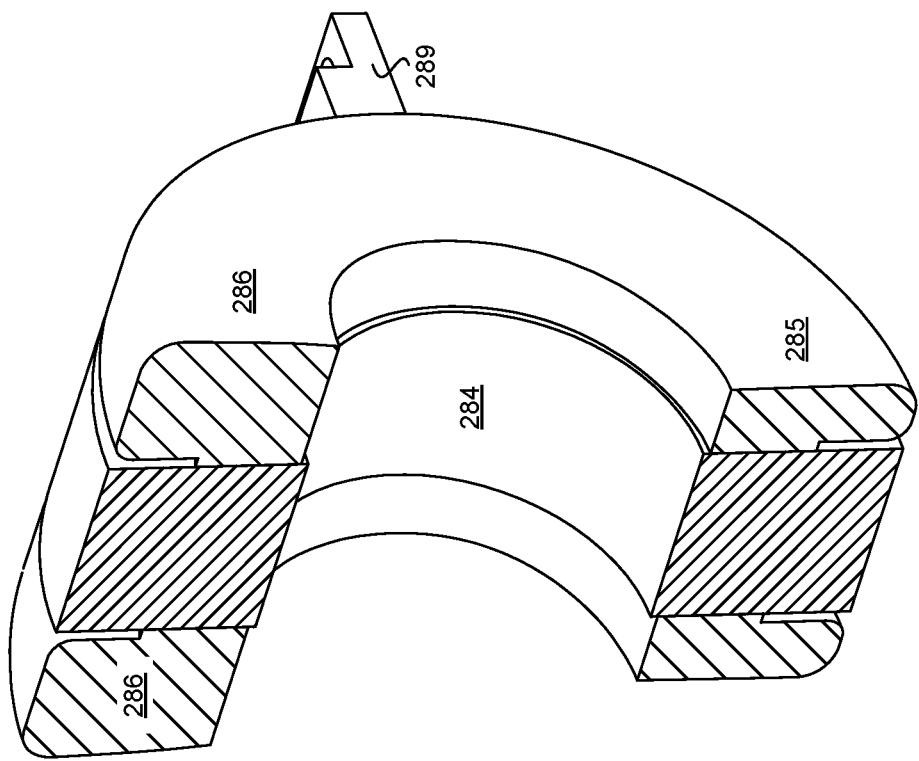

FIG. 16A illustrates a perspective view of a hybrid stator 283 with coils of a lift electromagnet integrated with stator coils (stator and lift coils 286), and FIG. 16B illustrates a side cross section view of FIG. 16A. The integrated coils can either be the same coils for lifting and rotation, or separation electrical connections on the coils for lifting and the coils for rotation.

Figure 17B:
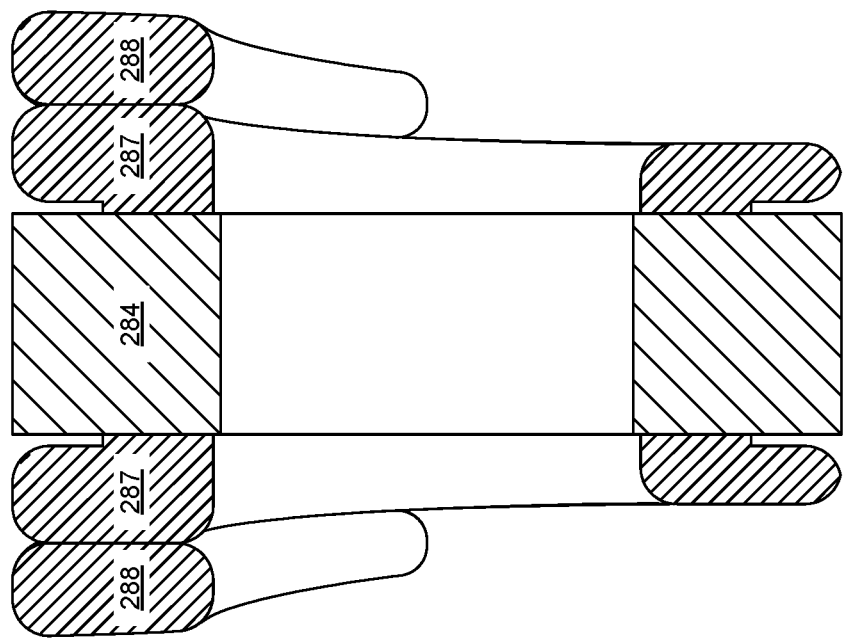
FIGS. 17A-17B illustrate views of an example stator with coils of a lift electromagnet.
Figure 17A:
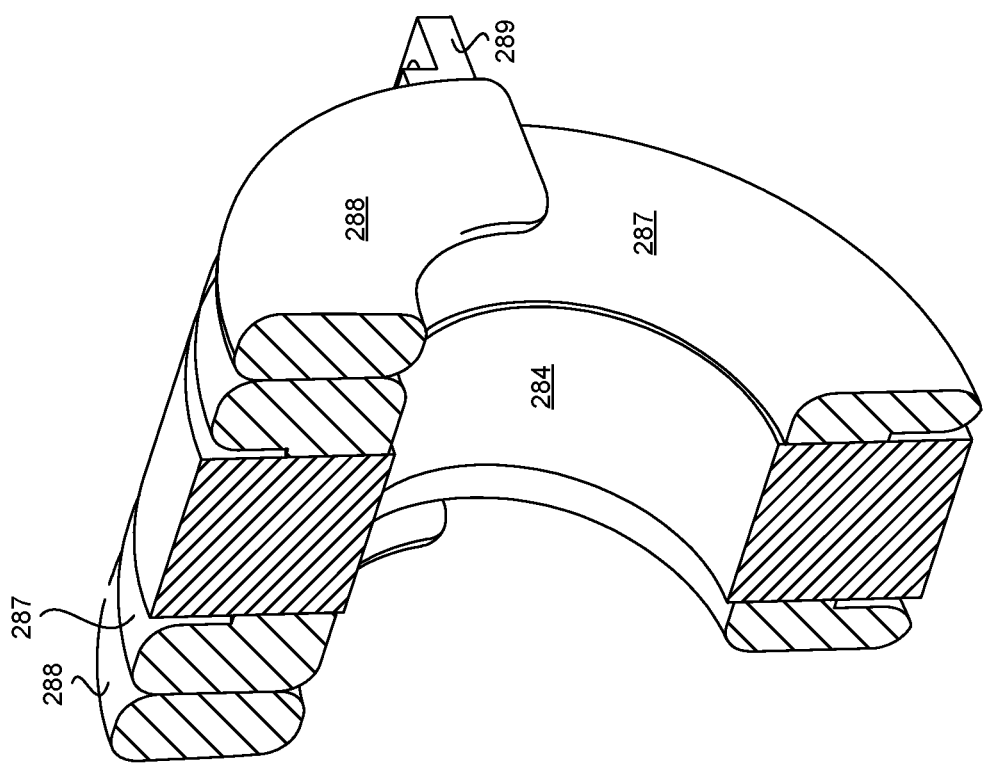

FIG. 17A illustrates a perspective view of a hybrid stator with coils 288 of a lift electromagnet and stator coils 289, and FIG. 17B illustrates a side cross section view of FIG. 17A. The lift coils provide lifting on one side of the stator and stator coils provide rotation for the rotor.

Figure 18A:
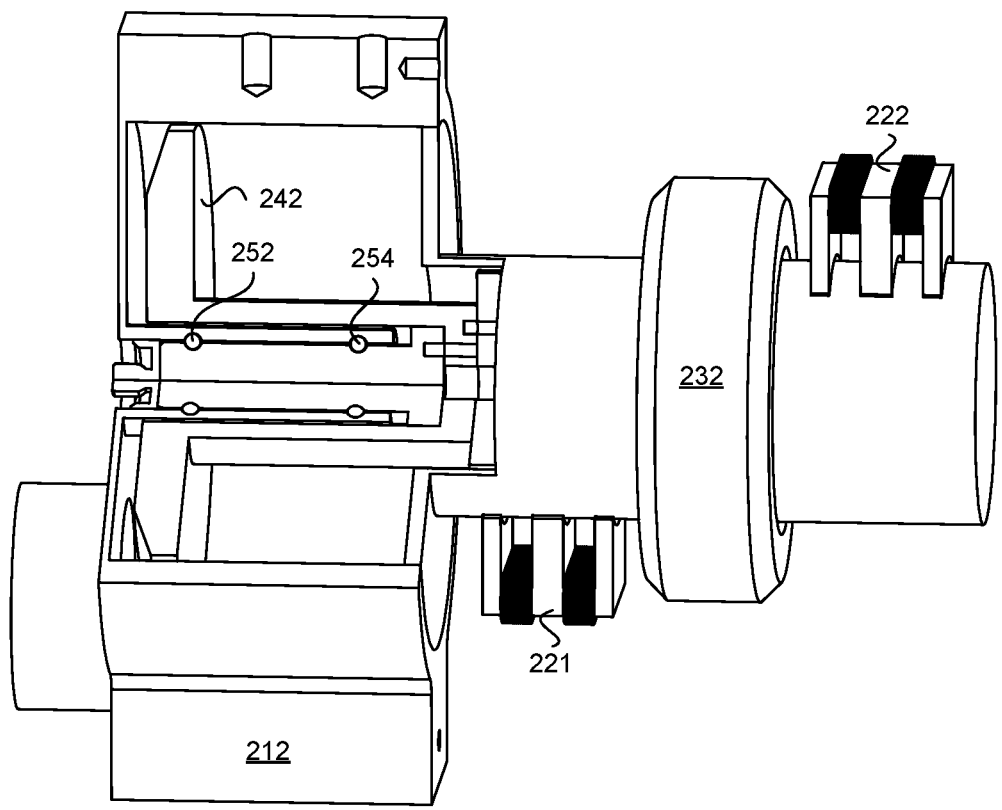
FIGS. 18A-18B illustrate views of an example anode assembly of an x-ray tube with a lift electromagnet and a secondary lift electromagnet.
Figure 18B:
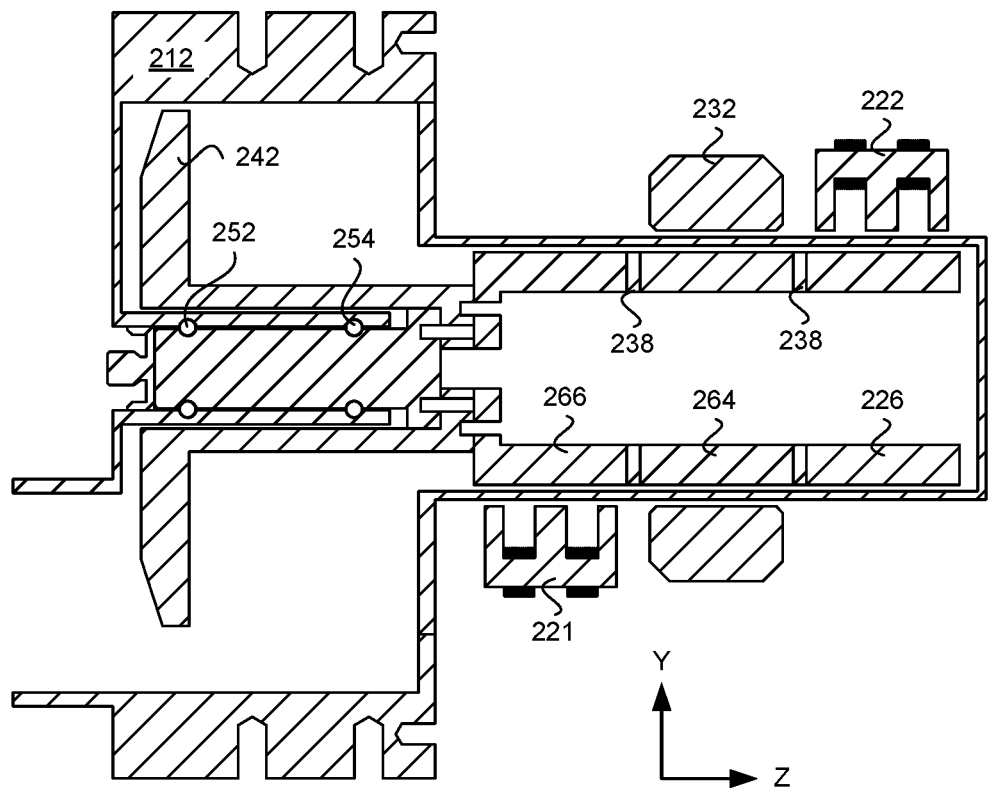

FIG. 18A illustrates a perspective view of an anode assembly of an x-ray tube with a lift electromagnet 222 and a secondary lift electromagnet 221, and FIG. 18B illustrates a side cross section view of FIG. 18A. The use of multiple electromagnets can be used to artificially shift the center of gravity of the anode assembly. An ideal location to lift on an anode assembly is at the center of gravity of the anode assembly. However, the center of gravity is typically located inside or near the target where due to thermal reasons and space constraints the anode can be difficult to lift. As a result, for example, the lift electromagnet can put a greater force or stress on one bearing race 254 (acting as a fulcrum) relative to another bearing race 252. The use of two magnets, the lift electromagnet and the secondary lift electromagnet, can assist in balancing the lift force on the bearings. The use of two magnets can allow for more complicated behavior and more degrees of freedom in the movement and force on the anode assembly and bearings. The secondary lift electromagnet located close to the center of gravity can apply a force opposing the g-force and reduce the load on the bearings. The lift electromagnet magnet located farther away from the center of gravity can pull in the opposite direction from the secondary lift electromagnet and provide the balancing force to help provide equal loading on each bearing race. The additional lift electromagnets can add additional length to the x-ray tube profile (along the z-axis).

The lift electromagnet can have various coil or winding configurations. For example, the coils can be add on the pole ends (e.g., inner pole ends or outer pole ends) or on the core web between the pole ends. FIGS. 19A-21B illustrate lift electromagnets with various coil configurations. Adding coils to the outer pole ends 322 can add additional length to the x-ray tube profile, which may be undesirable.

Figure 19A:
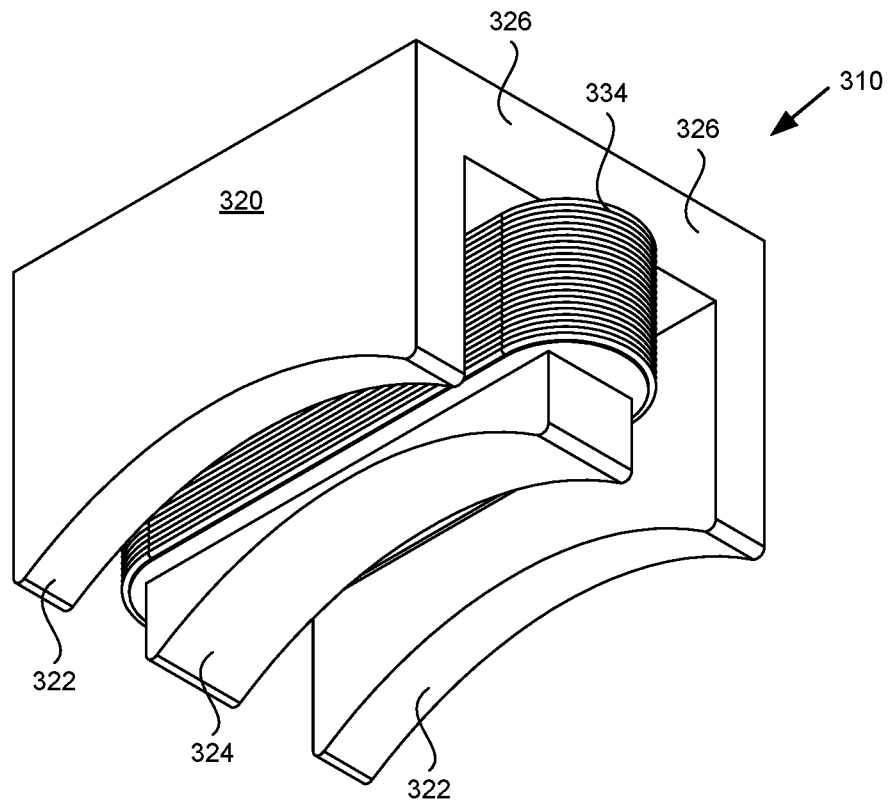
FIGS. 19A-19B illustrate views of an example three-pole lift electromagnet with coils around an inner pole end.
Figure 19B:
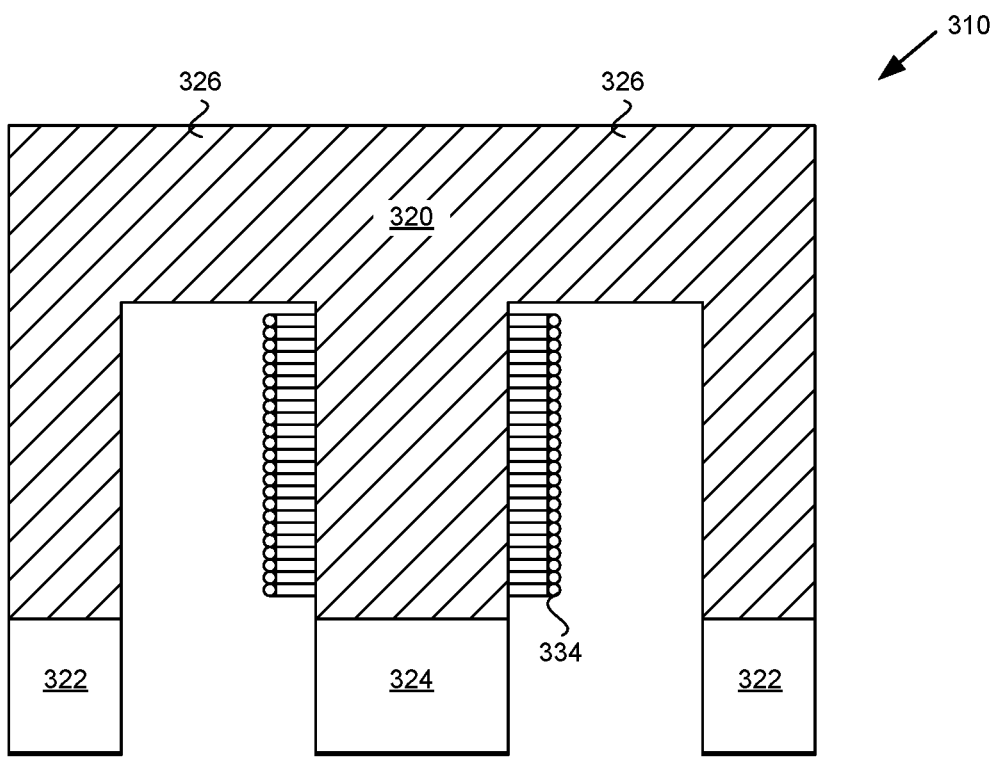

FIG. 19A illustrates a perspective view of a three-pole lift electromagnet 310 with coils 334 around an inner pole end 324, and FIG. 19B illustrates a side cross section view of FIG. 19A. A benefit of having the coil around an inner pole end is that the coil is contained inside the volume of the magnet core 320. Therefore, the magnet core volume can be maximized such that the lift electromagnet can handle more magnetic flux before saturating. A disadvantage is that the magnetic flux may only be controlled in one pole of the three poles. For example, more magnetic flux may exist in one of the outer poles than the other outer pole (due to the distance between each outer pole and the lift shaft or other factors), so the lift may not be balanced across the lift electromagnet. As a result, the lift force may be applied in an suboptimal location.

Figure 20A:
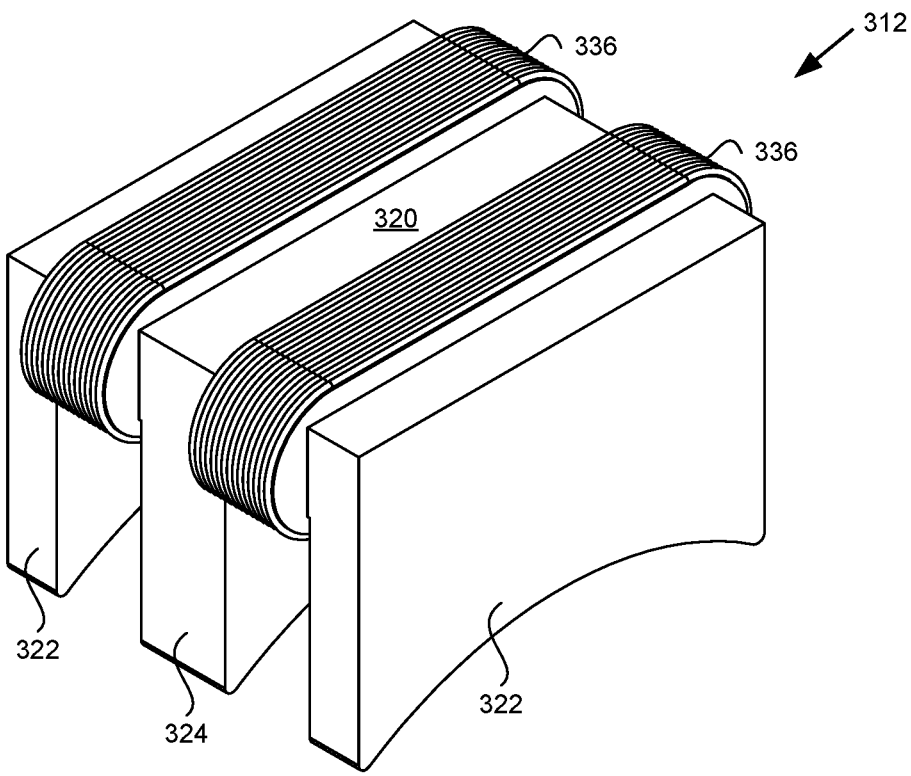
FIGS. 20A-20B illustrate views of an example three-pole lift electromagnet with coils around core webs between the pole ends.
Figure 20B:
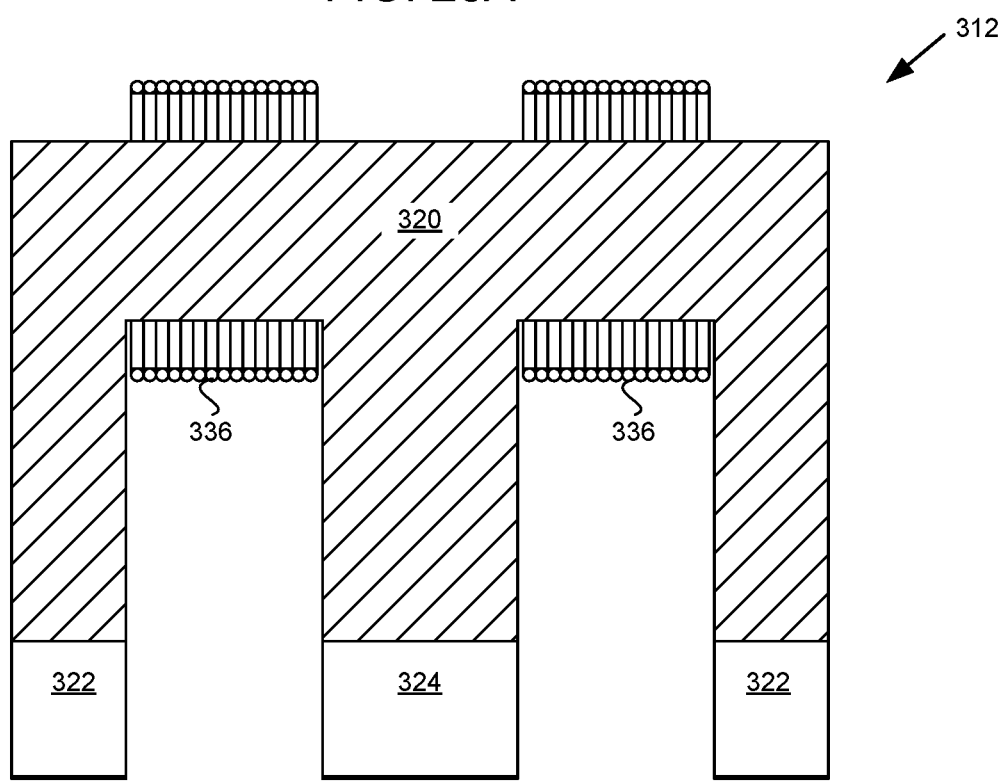

FIG. 20A illustrates a perspective view of a three-pole lift electromagnet 312 with coils 336 around core webs 326 between the pole ends 322 and 324, and FIG. 20B illustrates a side cross section view of FIG. 20A. With core web coils, the flux can balanced equally in the magnet, especially if the coils have equal number of turns and similar current. However, half of each of the core web coils is outside the magnet core 320 so the core web coil protruding from the magnet core may reduce the size of the magnet core when the tube housing constrains the space allowed for the lift electromagnet. Therefore, for the same volume this coil pack variation results in a smaller magnetic core and less flux capacity than the single middle coil.

Figure 21A:
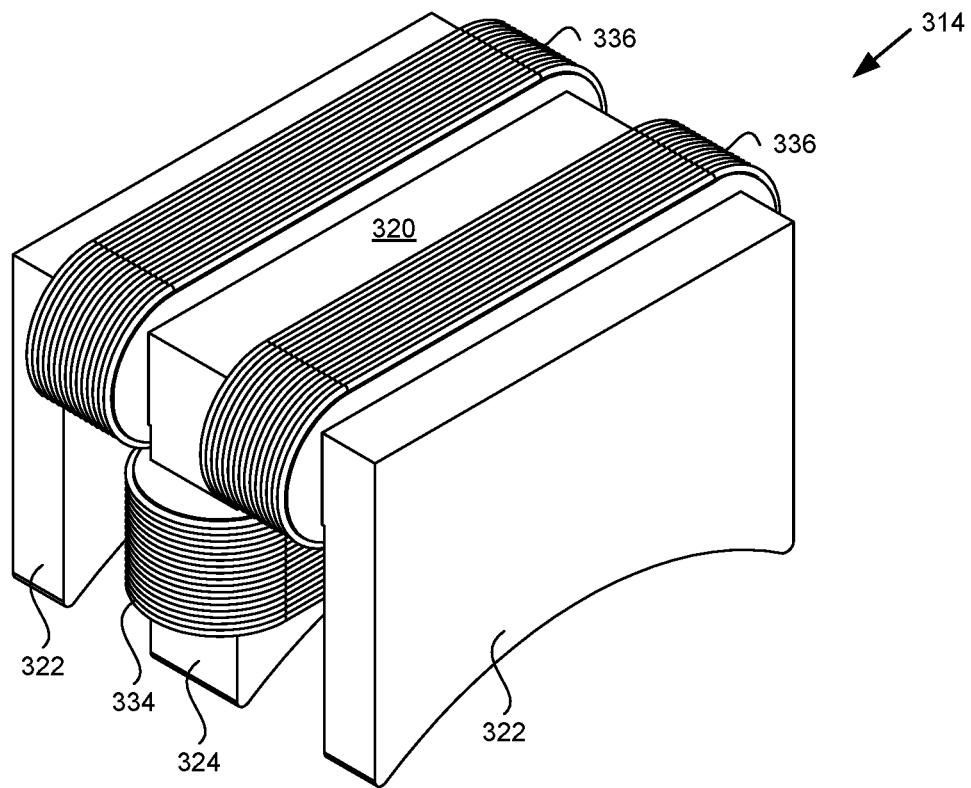
FIGS. 21A-21B illustrate views of an example three-pole lift electromagnet with coils around an inner pole end and core webs between the pole ends.
Figure 21B:
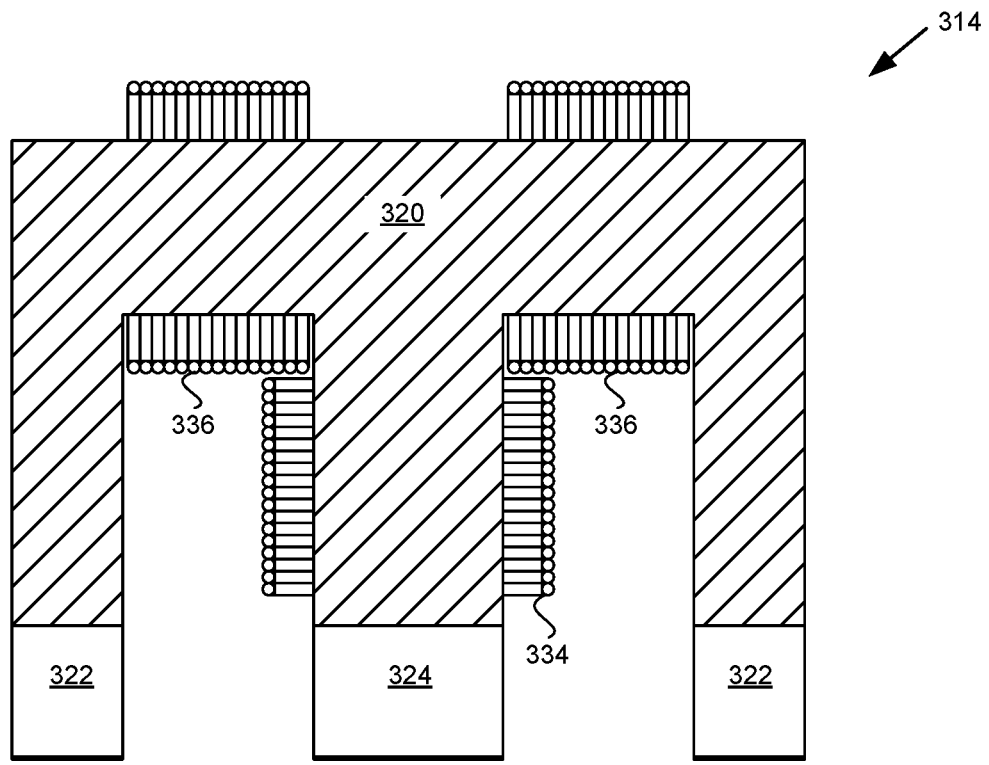

FIG. 21A illustrates a perspective view of a three-pole lift electromagnet 314 with coils 334 and 336 around an inner pole end 324 and core webs 326 between the pole ends, and FIG. 21B illustrates a side cross section view of FIG. 21A. The lift electromagnet 314 is a hybrid between the lift electromagnet 310 and the lift electromagnet 312. Having additional coils allows for more degrees of freedom in optimizing the lift electromagnet with the coil turn count and overall volume optimization. For example, the three different coils of the lift electromagnet can have turn counts that maximize magnet performance and force with equal magnetic flux through the various poles of the magnet while still maintaining a relatively small size.

The magnetic lift device can either be passive (e.g., permanent magnet) or active (e.g., electromagnet). Examples of active means include electromagnetic or inductive forces. An example of a passive means include a supporting bearing that is loaded with a force opposite to the direction of the gantry force or a permanent magnet that loads the bearing opposite to the gantry force. One or multiple magnetic lift devices, which can include permanent magnets and electromagnets, can be used as a force offsetting device.

As the gantry force is not constant (stationary when not operational, ramping up during startup or ramping down during shut down, or at a specified gantry speed), the lift force may also vary to adapt to the variable gantry forces. The applied current to lift electromagnet may be varied controlled by a controlled module, control system, or control unit, such as a tube control unit (TCU) 450, shown in FIG. 24. The lift electromagnet can activated by AC or DC in the windings of the lift electromagnet. The lift electromagnet and ferromagnetic shaft can be adapted for AC or DC. The TCU can include a lift driver 452 to generate the current for the lift magnet. In some examples, the TCU can be integrated with the x-ray tube, or in other examples the TCU can be a separate component from the x-ray tube. The TCU can be located on the rotating gantry frame or on a stationary component, such as the stationary gantry frame.

Figure 24:
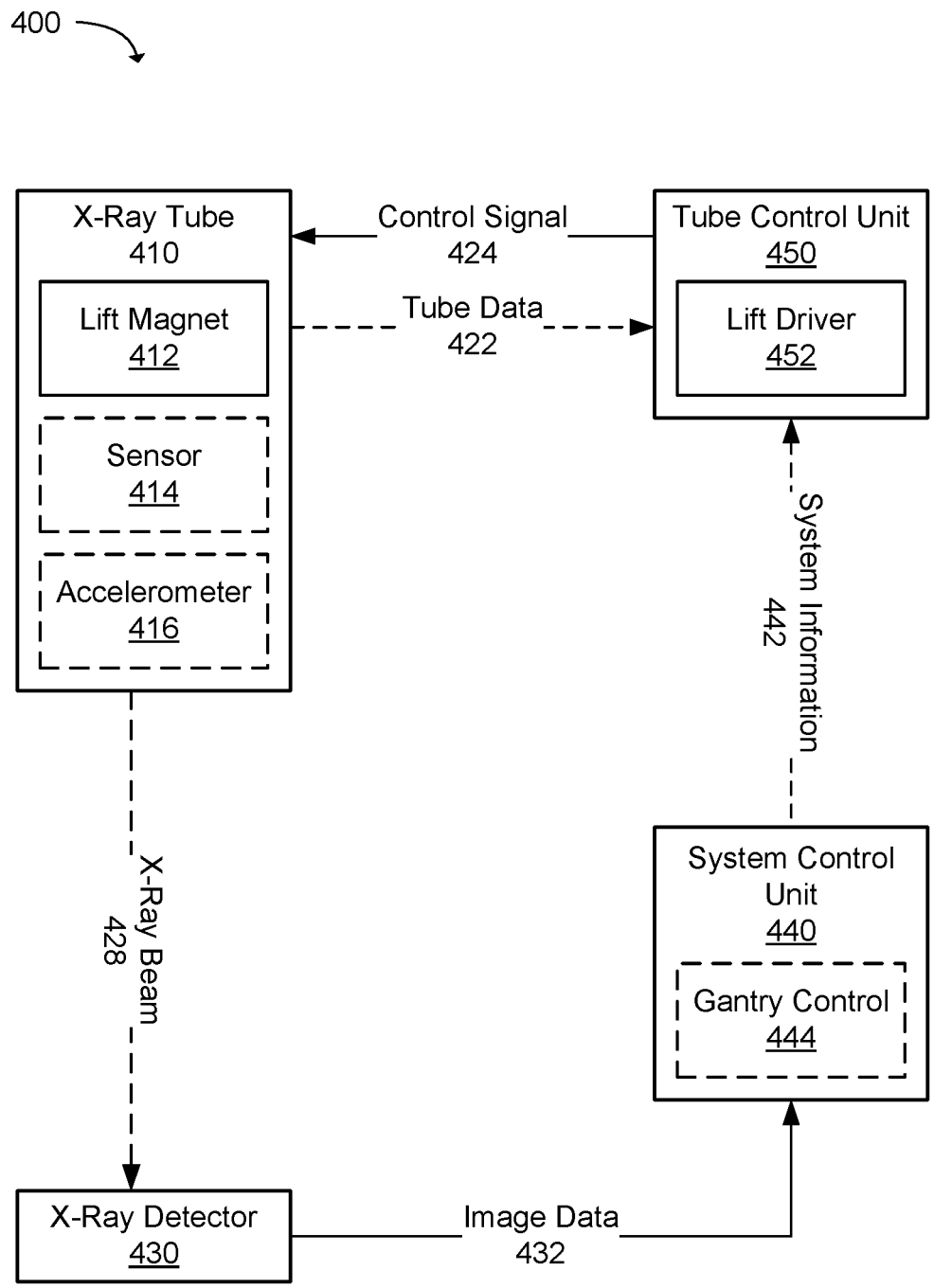
FIG. 24 illustrates a block diagram of an example x-ray system including an x-ray tube, a tube control unit (TCU), an x-ray detector, and a system control unit.

FIG. 24 illustrates some components of an example x-ray system 400 (e.g., rotating x-ray system). The x-ray system includes an x-ray tube 410 that generates an x-ray beam 428 and includes the lift magnet 412, a TCU 450 that can provide some control functions to the x-ray tube, an x-ray detector 430 to detect the x-rays beam and generates image data 432, and a system control unit 440 that can provide general control of and system information 442 (e.g., parameters) to the components of the x-ray system (e.g., x-ray tube, TCU, x-ray detector, and gantry). The system control unit may provide gantry control 444, which can include gantry speed. In one example, the system control unit can provide that system information to the TCU. The TCU or the system control unit can use the system information to calculate a gantry force on the bearing assembly of the x-ray tube. Based on the loading force, which includes the gantry force, the TCU can generate a lift force to offset or counter the loading force. In one example, the TCU can be integrated with the x-ray tube. In another example, the TCU can be a separate component from the x-ray tube. In some examples, the TCU can include other functionality related to the x-ray tube, such as steering and focusing.

In another example, the x-ray tube includes a sensor 414 to measure a parameter of the anode assembly which can be used to determine a loading force, a gantry force, or a lift force. The sensor can provide dynamic feedback during operation of the x-ray system. Example sensors can include: a Hall sensor in close proximity to a pole end of the lift electromagnet used to measure magnetic flux of the lift electromagnet; a current sensor coupled to windings of the of the lift electromagnet used to measure a current of the windings of the lift electromagnet; a voltage sensor coupled to windings of the of the lift electromagnet used to measure a resistance of the windings of the lift electromagnet; a displacement sensor or an ultrasonic sensor used to measure a distance of a gap between the lift electromagnet and the ferromagnetic shaft or a deflection in the ferromagnetic shaft; an accelerometer 416 used to measure a vibration in the anode assembly, a centrifugal force, or a rotor force; a temperature sensor or thermocouple coupled to the windings or a core of the of the lift electromagnet used to measure a temperature of the windings or the core of the lift electromagnet; or a force sensor used to measure a force on the bearing assembly.

In an example, the TCU and x-ray tube can provide sensor feedback independent of system information from the system control unit or gantry control. The sensors can provide measurements, in which the loading force, the gantry force, or the lift force can be derived and the TCU can adjust the current to the lift electromagnet to adjust to the changing conditions of the loading force, the gantry force, or the lift force.

Figure 25:
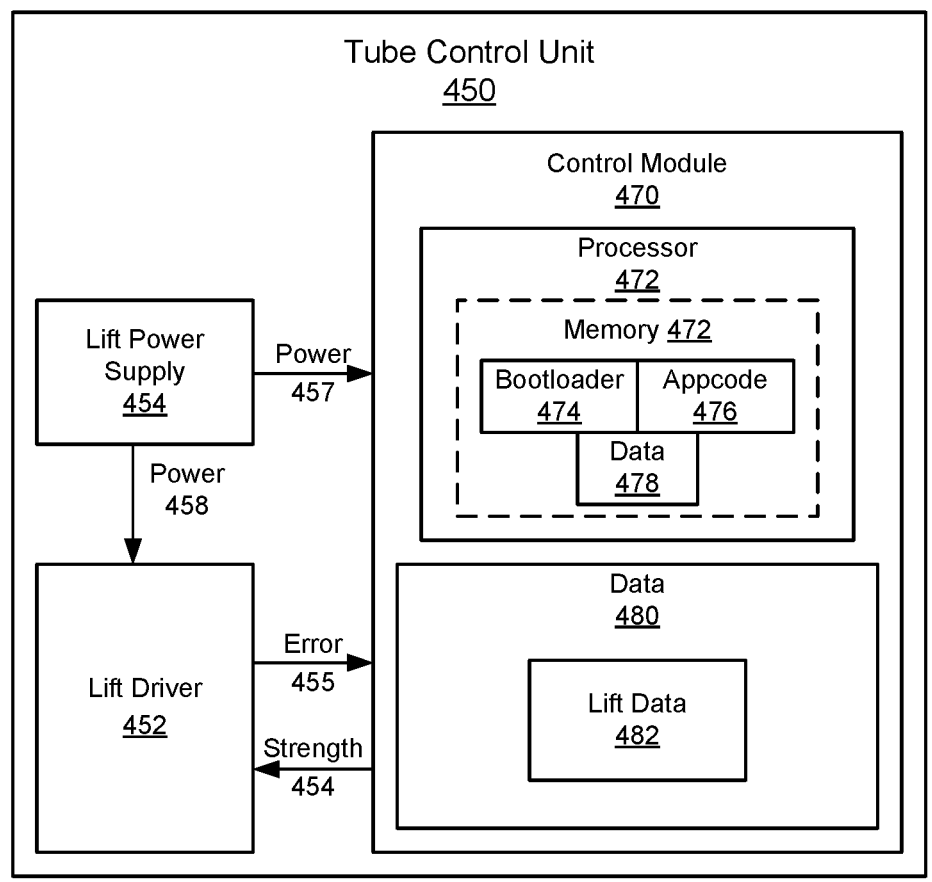
FIG. 25 illustrates a block diagram of an example tube control unit (TCU) and a system control unit.

FIG. 25 illustrates an example control system to control the lift electromagnet. The control system includes a TCU 450 with a lift power supply 454 that provides power 457 and 458 to a control module 470 and the lift driver 452. The control module 470 includes a processor 472 (e.g., controller or microprocessor) and data storage 480 that can include lift data 482. The processor includes memory 472 that includes bootloader code 472 to initialize the TCU, appcode 476 to run TCU application, and data memory 478 for processing data. The control module can send strength signals 454 to the lift driver for generating a lift current and receive error signals from the lift driver.

The applied magnetic force can be controlled by electrical power from the TCU, which can control current in the lift electromagnet, a distance of the lift electromagnet to the ferromagnetic shaft, or a combination of these approaches.

Although a permanent magnet can be used to provide a lift force, a permanent magnet provides a constant force with a fixed distance from the lift shaft, which does not allow for varying the lift force based on changing gantry speeds (which changes the gantry force) without adjusting the distance between the permanent magnet and lift shaft. A permanent magnet is an object made from a material that is magnetized and creates its own persistent magnetic field.

If permanent magnets are used, the magnetic force on the ferromagnetic shaft can be controlled by distance, temperature, magnet element orientation, gap, or interposed materials in the case of a magnet array, such as a Halbach array. A Halbach array is a special arrangement of magnets that augments the magnetic field on one side of the array while cancelling the field to near zero on the other side of the array.

Figure 26:
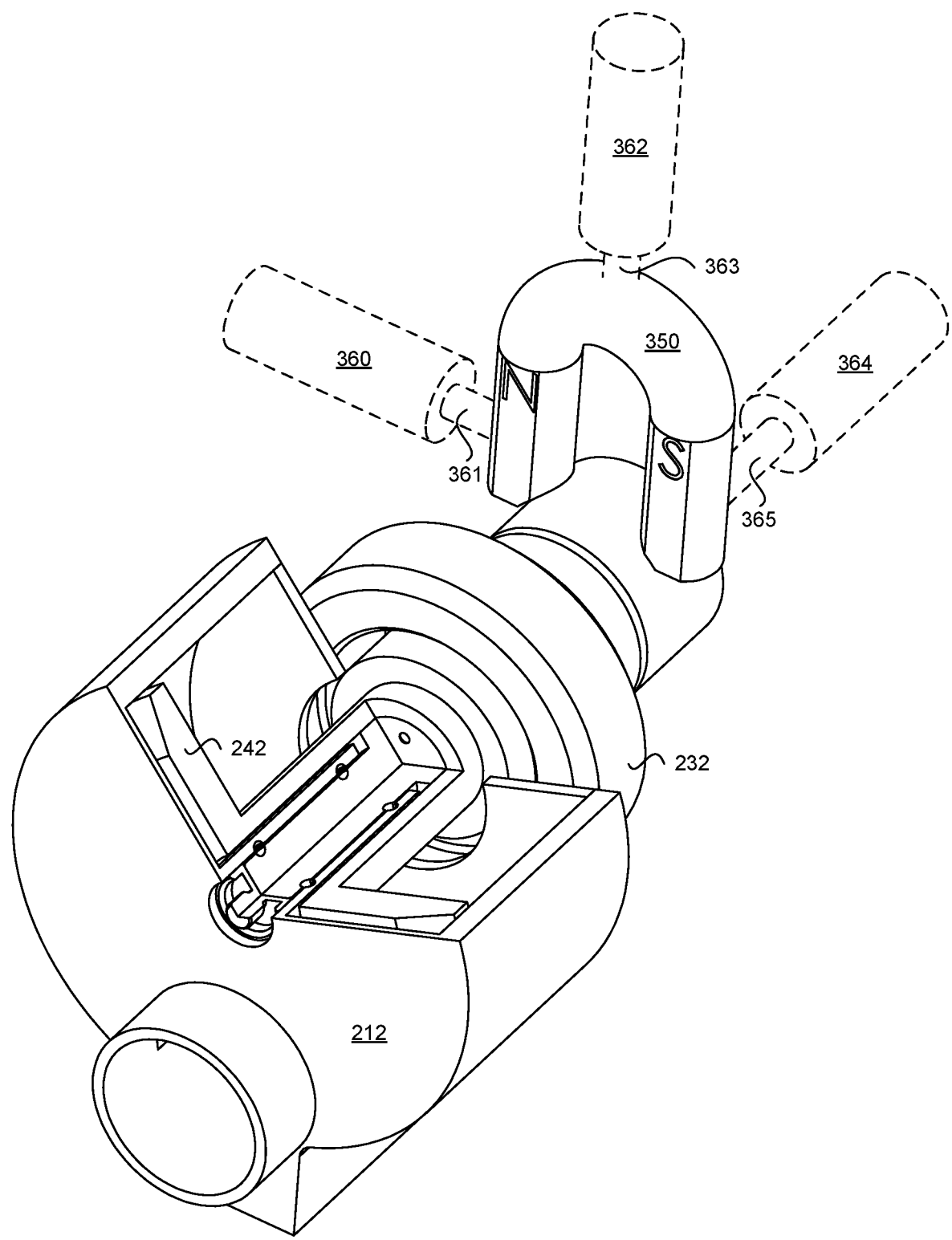
FIG. 26 illustrates a perspective section view of an example insert of an x-ray tube and a lift magnet with actuators.

FIG. 26 illustrates an x-ray tube using a permanent magnet 350 as a lift magnet with actuators. The actuators can change the lift gap, which can change the force on the lift shaft. The actuators can be used to change the lift force based on the gantry speed or loading of on the bearing assembly. The lift magnet can be coupled to an x-axis actuator 360 via an x-axis movable shaft 361, an y-axis actuator 362 via an y-axis movable shaft 363, or an z-axis actuator 364 via an z-axis movable shaft 365. The x-axis actuator, the y-axis actuator, or the z-axis actuator can be coupled to the tube housing, and the x-axis movable shaft, the y-axis movable shaft, or the z-axis movable shaft can be coupled to the permanent magnet. In another example, the movable shaft can be coupled to the tube housing and the actuator housing can be coupled to the permanent magnet.

In another example, lift permanent magnets may be used in combination with the lift electromagnet.

Method of Controlling a Lift Electromagnet

Figure 27:
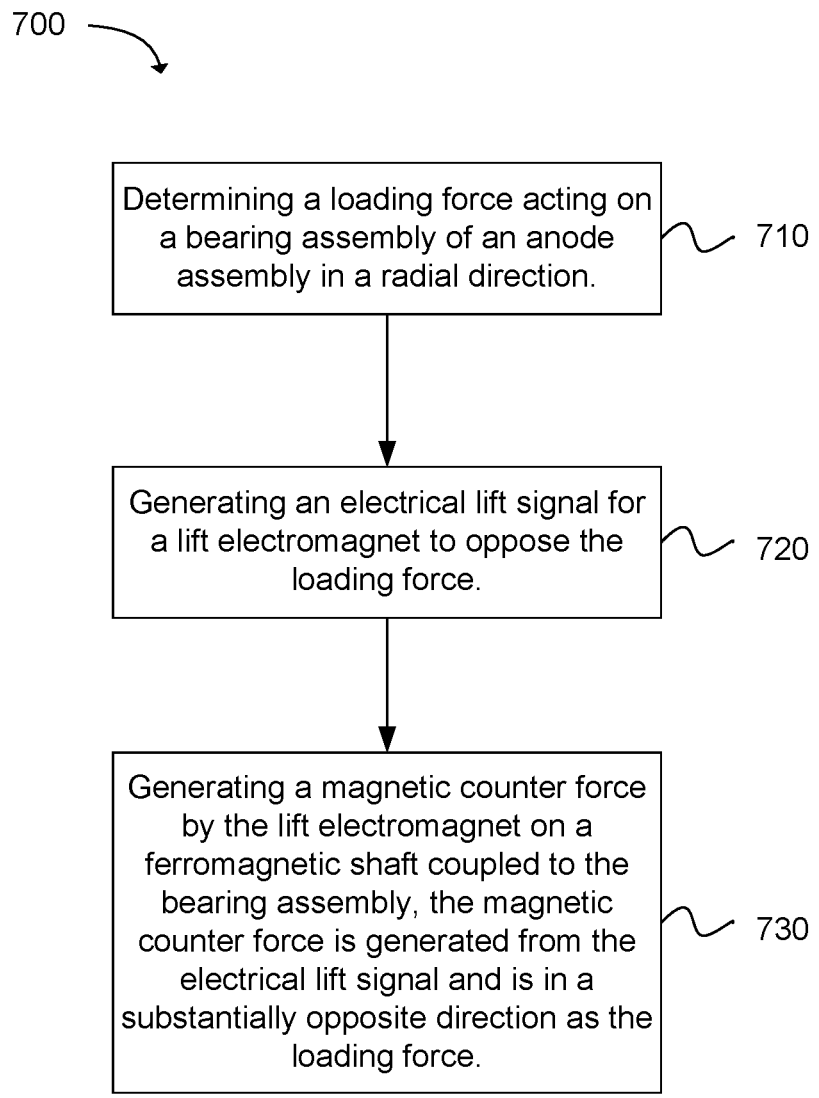
FIG. 27 is flowchart illustrating an example of a method of controlling a lift electromagnet in an anode assembly of an x-ray tube.

The flowchart shown in FIG. 27 illustrates a method 600 of controlling a lift electromagnet on an anode assembly of an x-ray tube. The method includes the step of determining a loading force acting on a bearing assembly of an anode assembly in a radial direction, as in step 610. The step of generating an electrical lift signal for a lift electromagnet to oppose the loading force follows, as in step 620. The next step of the method includes generating a magnetic counter force by the lift electromagnet on a ferromagnetic shaft coupled to the bearing assembly, as in step 630. The magnetic counter force is generated from the electrical lift signal and is in a substantially opposite direction as the loading force.

The technology (devices, assemblies, components, systems, and methods) described herein resolves many of the challenges with conventional bearing assemblies of x-ray tubes in rotating x-ray system, especially those that generate high g-force conditions. The technology described can offset, dampen, reduce, or balance the forces (including centrifugal force of the gantry) on the bearing assembly or anode assembly. The technology described can reduce vibration or noise, increase bearing life, increase the bearing load capability, control thermal contact, improve the centering and precision of the rotating assembly, and allow the use of smaller bearings (e.g., ball bearings or other rotating bearings) or use other bearing types in a rotating type x-ray tube (e.g., rotating anode type x-ray tube).

Using at least one of the examples described, the x-ray tube mounted on the rotating gantry frame at a radius of 0.7 meters from the center of axis, rotating at 0.275 sec/rot (~37 gs), and using a lift electromagnet, the number of rotations on the bearings was at least 3 times (i.e., life of the bearing assembly was extended by 3 times over) a conventional life of the bearing assembly on an x-ray tube without a lift electromagnet before the bearings failed. For the x-ray tube mounted on the rotating gantry frame at a radius of 0.7 meters from the center of axis, experiencing approximately 50 gs, and using a lift electromagnet, the life of the bearing assembly was 2 times a bearing assembly of an x-ray tube without a lift electromagnet experiencing 37gs before the bearings failed. Thus, the use of the lift electromagnet can extend the life of the bearing assembly in an anode assembly and by extension the life of the x-ray tube.

In one example, an anode assembly includes an anode 242, a bearing assembly 250, a ferromagnetic shaft 226, and a lift electromagnet 222. The anode is configured to receive electrons emitted by a cathode. The bearing assembly is configured to stabilize the anode during a rotation of the anode. The ferromagnetic shaft is coupled to the anode and has an axis of rotation that is substantially collinear with an axis of rotation of the anode. The lift electromagnet is configured to apply a magnetic force to the ferromagnetic shaft in a radial direction.

In another example, the lift electromagnet includes at least three pole ends oriented towards the ferromagnetic shaft. The windings (or coils) of the lift electromagnet can be located on at least one core web between the poles 336, on an inner pole end 334, or on the at least one core web 336 and the inner pole end 334. The ferromagnetic shaft can include a slotted shaft 226A or a laminated shaft 226B. The lift electromagnet is activated by alternating current (AC) or direct current (DC) in windings of the lift electromagnet. The anode assembly can further include a stator 232 at least partially surrounding a rotor sleeve 234 coupled to the anode, wherein the rotor sleeve is configured to rotate in response to applied electromagnetic fields on the stator, and the windings of the lift electromagnet at least partially surround a core of the stator. The bearing assembly can include a ball bearing assembly with at least one race 252 or 254, a roller element bearing, a plain bearing, a sleeve bearing 247 and 257, a journal bearing, or liquid metal bearing.

In another example, the anode assembly can further include a control module 470 configured to vary the magnetic force on the ferromagnetic shaft. The anode assembly can further include a sensor 414 to detect the magnetic force on the ferromagnetic shaft. The control module is configured to vary a current applied to the lift electromagnet base on a sensor value. The sensor can include an ammeter or voltage meter coupled to the windings of the lift electromagnet, a Hall sensor in close proximity to a pole end of the lift electromagnet, an ultrasonic sensor, or displacement sensor.

In another configuration, the anode assembly can further include a rotor sleeve coupled to the anode. The rotor sleeve 234 can be configured to rotate in response to applied electromagnetic fields.

In another example, the lift electromagnet 222 or 291 is co-planar with the stator 233 or 296 relative to the axis of rotation of the ferromagnetic shaft. The anode assembly can further include a sector stator 296 partially surrounding a rotor sleeve coupled to the anode. The rotor sleeve is configured to rotate in response to applied electromagnetic fields on the sector stator, and the lift electromagnet 291 is co-planar with the sector stator relative to the axis of rotation of the ferromagnetic shaft. The sector stator can partially surround the rotor sleeve between 180° and 350°.

In another example, an x-ray tube includes an evacuated enclosure, a cathode disposed within the evacuated enclosure, an anode disposed within the evacuated enclosure configured to receive electrons emitted by the cathode, a bearing assembly 250 configured to stabilize the anode during a rotation of the anode, a stator 232 configured to generate electromagnetic fields, a rotor sleeve 234 coupled to the anode, where the rotor sleeve is configured to rotate in response to applied electromagnetic fields from the stator, a ferromagnetic shaft 226 coupled to the anode and having an axis of rotation that is substantially collinear with an axis of rotation of the anode, and a lift electromagnet 222 configured to apply a magnetic force to the ferromagnetic shaft in a radial direction.

In another example, the lift electromagnet includes at least three pole ends oriented towards the ferromagnetic shaft. The pole ends of the lift electromagnet can extend through an envelope of the evacuated enclosure (FIG. 8). In another configuration, the lift electromagnet is disposed within the evacuated enclosure (FIG. 9). In another configuration, the lift electromagnet 222 is co-planar with the stator 233 relative to the axis of rotation of the ferromagnetic shaft, and the stator is positioned outside the evacuated enclosure. In another configuration, the lift electromagnet 222 is positioned between the bearing assembly 250 and the stator 232 relative to the axis of rotation of the ferromagnetic shaft (FIG. 12A-12B).

In another example, the x-ray tube further includes a tube control unit (TCU) 450 configured to vary the magnetic force on the ferromagnetic shaft. The x-ray tube can further include a sensor to detect the magnetic force on the ferromagnetic shaft. The tube control unit is configured to vary a current applied to the lift electromagnet base on a sensor value. The x-ray tube can further include an accelerometer disposed in the x-ray tube to determine a force on the bearing assembly. The tube control unit can be configured to calculate an anode rotational speed based on an accelerometer value from the accelerometer.

In another example, an x-ray system includes an rotatable annular gantry 200, an x-ray tube as previously described coupled to the rotatable gantry, and an x-ray detector coupled to the rotatable gantry and configured to detect x-ray radiation from the x-ray detector. The tube control unit can be configured to calculate a gantry force on the bearing assembly or a gantry rotational speed based on an accelerometer value from the accelerometer.

In another example, an x-ray system includes an rotatable annular gantry, an x-ray tube as previously described coupled to the rotatable gantry, a system control unit configured to provide control of the rotatable gantry and send system data to the TCU, and the TCU or the system control unit calculates a force on the bearing assembly based on gantry data, and the TCU varies the magnetic force proportional to the force on the bearing assembly. The x-ray system can further include an x-ray detector couple to the rotatable gantry and configured to detect x-ray radiation from the x-ray detector.

In another example, a method of controlling a lift electromagnet on an anode assembly of an x-ray tube can include determining a loading force acting on a bearing assembly of an anode assembly in a radial direction. The step of generating an electrical lift signal for a lift electromagnet to oppose the loading force can follow. The next step of the method includes generating a magnetic counter force by the lift electromagnet on a ferromagnetic shaft coupled to the bearing assembly. The magnetic counter force is generated from the electrical lift signal and is in a substantially opposite direction as the loading force.

The method can further include rotating a rotatable gantry frame. The anode assembly is coupled to a x-ray tube and the x-ray tube is coupled to the rotatable gantry frame, and the rotation of the rotatable gantry frame adds a centrifugal force from the gantry to the loading force. The step of determining the loading force can further include calculating the centrifugal force based on the rotation speed of the rotatable gantry frame.

In another example, method can further include sensing, using a sensor, a parameter of the anode assembly. The step of determining the loading force further comprises calculating the loading force or the magnetic counter force using the parameter. The sensor can be a Hall sensor in close proximity to a pole end of the lift electromagnet and the parameter is a magnetic flux measurement of the lift electromagnet, or the sensor can be a current sensor coupled to windings of the of the lift electromagnet and the parameter is a current measurement of the windings of the lift electromagnet, or the sensor can be a voltage sensor coupled to windings of the of the lift electromagnet and the parameter is a resistance measurement of the windings of the lift electromagnet, or the sensor can be a displacement sensor or an ultrasonic sensor and the parameter is a distance measurement of a gap between the lift electromagnet and the ferromagnetic shaft, or the sensor can be an accelerometer and the parameter is a vibration in the anode assembly, the centrifugal force, or a rotor force, or the sensor can be a temperature sensor or thermocouple coupled to the windings or a core of the of the lift electromagnet and the parameter is a temperature measurement of the windings or the core of the lift electromagnet, or the sensor can be a force sensor and the parameter is a force measurement on the bearing assembly.

The step of generating the electrical lift signal can further include generating a lift current for windings of the of the lift electromagnet. The step of generating the magnetic counter force can vary with changes in the loading force.

In another example, anode assembly for an x-ray tube includes an anode configured to receive electrons emitted by a cathode, a bearing assembly configured to stabilize the anode during a rotation of the anode, a ferromagnetic shaft coupled to the anode and having an axis of rotation that is substantially collinear with an axis of rotation of the anode, and a lift magnet (e.g., permanent magnet 350) configured to apply a magnetic force to the ferromagnetic shaft in a radial direction.

All references recited herein are incorporated herein by specific reference in their entirety.

Reference throughout this specification to an "example" or an "embodiment" means that a particular feature, structure, or characteristic described in connection with the example is included in at least one embodiment of the invention. Thus, appearances of the words an "example" or an "embodiment" in various places throughout this specification are not necessarily all referring to the same embodiment.

Furthermore, the described features, structures, or characteristics may be combined in a suitable manner in one or more embodiments. In the following description, numerous specific details are provided (e.g., examples of layouts and designs) to provide a thorough understanding of embodiments of the invention. One skilled in the relevant art will recognize, however, that the invention can be practiced without one or more of the specific details, or with other methods, components, layouts, etc. In other instances, well-known structures, components, or operations are not shown or described in detail to avoid obscuring aspects of the invention.

While the forgoing examples are illustrative of the principles of the invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited. Various features and advantages of the invention are set forth in the following claims.

What is claimed is:

1. An anode assembly for an x-ray tube, comprising:
    an anode configured to receive electrons emitted by a cathode;
    a bearing assembly configured to stabilize the anode during a rotation of the anode;
    a ferromagnetic shaft coupled to the anode and having an axis of rotation that is substantially collinear with an axis of rotation of the anode; an envelope of an evacuated enclosure; and
    a lift electromagnet comprising pole ends that extend through the envelope of the evacuated enclosure.

2. The anode assembly of claim 1, further comprising windings located on at least one core web between the poles of the lift electromagnet, on an inner pole end, or on the at least one core web and the inner pole end.

3. The anode assembly of claim 1, wherein the ferromagnetic shaft includes a slotted shaft or a laminated shaft.

4. The anode assembly of claim 1, wherein the lift electromagnet is activated by alternating current (AC) or direct current (DC) in windings of the lift electromagnet.

5. The anode assembly of claim 1, wherein the bearing assembly includes a ball bearing assembly with at least one race, a roller element bearing, a plain bearing, a sleeve bearing, a journal bearing, or liquid metal bearing.

6. The anode assembly of claim 1, further comprising:
    a control module configured to vary the magnetic force on the ferromagnetic shaft.

7. The anode assembly of claim 1, further comprising:
    a rotor sleeve coupled to the anode, wherein the rotor sleeve is configured to rotate in response to applied electromagnetic fields.

8. The anode assembly of claim 1, further comprising:
    a sector stator partially surrounding a rotor sleeve coupled to the anode, wherein the rotor sleeve is configured to rotate in response to applied electromagnetic fields on the sector stator, and the lift electromagnet is co-planar with the sector stator relative to the axis of rotation of the ferromagnetic shaft.

9. The anode assembly of claim 6, further comprising:
    a sensor to detect the magnetic force on the ferromagnetic shaft, wherein the control module is configured to vary a current applied to the lift electromagnet based on a sensor value.

10. The anode assembly of claim 9, wherein the sensor includes an ammeter or voltage meter coupled to the windings of the lift electromagnet, a Hall sensor in close proximity to a pole end of the lift electromagnet, an ultrasonic sensor, or displacement sensor.

11. The anode assembly of claim 7, wherein the lift electromagnet is co-planar with the stator relative to the axis of rotation of the ferromagnetic shaft.

12. The anode assembly of claim 8, wherein the sector stator partially surrounds the rotor sleeve between 180° and 350°.

13. An x-ray tube, comprising:
    an evacuated enclosure;
    a cathode disposed within the evacuated enclosure;
    an anode disposed within the evacuated enclosure configured to receive electrons emitted by the cathode;
    a bearing assembly configured to stabilize the anode during a rotation of the anode;
    a stator configured to generate electromagnetic fields;

a rotor sleeve coupled to the anode, the rotor sleeve is configured to rotate in response to applied electromagnetic fields from the stator;

a ferromagnetic shaft coupled to the anode and having an axis of rotation that is substantially collinear with an axis of rotation of the anode; and a lift electromagnet configured to apply a magnetic force to the ferromagnetic shaft in a radial direction, wherein pole ends of the lift electromagnet extend through an envelope of the evacuated enclosure.

14. The x-ray tube of claim 13, wherein the lift electromagnet is co-planar with the stator relative to the axis of rotation of the ferromagnetic shaft, and the stator is positioned outside the evacuated enclosure.

15. The x-ray tube of claim 13, further comprising:
a tube control unit (TCU) configured to vary the magnetic force on the ferromagnetic shaft.

16. The x-ray tube of claim 13, further comprising:
an accelerometer disposed in the x-ray tube.

17. The x-ray tube of claim 15, further comprising:
a sensor to detect the magnetic force on the ferromagnetic shaft, wherein the tube control unit is configured to vary a current applied to the lift electromagnet based on a sensor value.

18. An x-ray system, comprising:
an rotatable annular gantry;
the x-ray tube of claim 16 coupled to the rotatable gantry; and
an x-ray detector coupled to the rotatable gantry and configured to detect x-ray radiation from the x-ray detector.

19. The x-ray system of claim 18, further comprising a tube control unit configured to calculate a gantry force on the bearing assembly or a gantry rotational speed based on an accelerometer value from the accelerometer.

20. A method of controlling a lift electromagnet in an anode assembly of an x-ray tube, the method comprising:

determining a loading force acting on a bearing assembly of an anode assembly in a radial direction;

generating an electrical lift signal for a lift electromagnet to oppose the loading force, the lift electromagnet including pole ends that extend through an envelope of an evacuated enclosure of the x-ray tube; and generating a magnetic counter force by the lift electromagnet on a ferromagnetic shaft coupled to the bearing assembly, the magnetic counter force is generated from the electrical lift signal and is in a substantially opposite direction as the loading force.

21. The method of claim 20, further comprising:
rotating a rotatable gantry frame, wherein the anode assembly is coupled to the x-ray tube and the x-ray tube is coupled to the rotatable gantry frame, and the rotation of the rotatable gantry frame adds a centrifugal force from the gantry to the loading force.

22. The method of claim 20, wherein generating the electrical lift signal further comprises:
generating a lift current for windings of the of the lift electromagnet.

23. The method of claim 20, wherein generating the magnetic counter force varies with changes in the loading force.

24. The method of claim 21, wherein determining the loading force further comprises:
calculating the centrifugal force based on the rotation speed of the rotatable gantry frame.

25. The method of claim 21, further comprising
sensing, using a sensor, a parameter of the anode assembly; and
wherein determining the loading force further comprises calculating the loading force or the magnetic counter force using the parameter.

* * * * *